US010555675B2

(12) United States Patent
Satish et al.

(10) Patent No.: US 10,555,675 B2
(45) Date of Patent: Feb. 11, 2020

(54) METHOD FOR PROJECTING BLOOD LOSS OF A PATIENT DURING A SURGERY

(71) Applicant: Gauss Surgical, Inc., Los Altos, CA (US)

(72) Inventors: Siddarth Satish, Cupertino, CA (US); Kevin Miller, Mountain View, CA (US); Titas De, Los Altos, CA (US)

(73) Assignee: Gauss Surgical, Inc., Menlo Park, CA (US)

( * ) Notice: Subject to any disclaimer, the term of this patent is extended or adjusted under 35 U.S.C. 154(b) by 500 days.

(21) Appl. No.: 15/154,921

(22) Filed: May 13, 2016

(65) Prior Publication Data

US 2016/0331248 A1    Nov. 17, 2016

Related U.S. Application Data

(60) Provisional application No. 62/162,128, filed on May 15, 2015.

(51) Int. Cl.
*A61B 5/02* (2006.01)
*A61B 5/00* (2006.01)

(52) U.S. Cl.
CPC ........ *A61B 5/02042* (2013.01); *A61B 5/0077* (2013.01)

(58) Field of Classification Search
None
See application file for complete search history.

(56) References Cited

U.S. PATENT DOCUMENTS

| | | |
|---|---|---|
| 2,707,955 A | 5/1955 | Borden |
| 3,182,252 A | 5/1965 | van den Berg |
| 3,199,507 A | 8/1965 | Kamm |
| 3,367,431 A | 2/1968 | Prindle Baker |
| 3,646,938 A | 3/1972 | Haswell |
| 3,832,135 A | 8/1974 | Drozdowski et al. |
| 3,864,571 A | 2/1975 | Stillman et al. |
| 3,948,390 A | 4/1976 | Ferreri |
| 4,105,019 A | 8/1978 | Haswell |
| 4,149,537 A | 4/1979 | Haswell |
| 4,244,369 A | 1/1981 | McAvinn et al. |

(Continued)

FOREIGN PATENT DOCUMENTS

| | | |
|---|---|---|
| CA | 2870635 A1 | 10/2013 |
| CN | 101505813 A | 8/2009 |

(Continued)

OTHER PUBLICATIONS

Non-Final Office Action dated Apr. 11, 2018, for U.S. Appl. No. 15/416,986, filed Jan. 26, 2017, 7 pages.

(Continued)

*Primary Examiner* — Michael R Bloch
(74) *Attorney, Agent, or Firm* — Schwegman Lundberg & Woessner, P.A.

(57) ABSTRACT

Systems for monitoring blood loss include a display for simultaneously depicting a current blood loss metric at different time points or along a time line. In addition, historical or comparative blood loss information is provided on the display so that the healthcare provider can see assess the current blood loss metric relative to other metrics, so that the healthcare provider can more accurately assess and manage the patient's status.

32 Claims, 11 Drawing Sheets

(56) References Cited

U.S. PATENT DOCUMENTS

| | | |
|---|---|---|
| 4,402,373 A | 9/1983 | Comeau |
| 4,422,548 A | 12/1983 | Cheesman et al. |
| 4,429,789 A | 2/1984 | Puckett |
| 4,562,842 A | 1/1986 | Morfeld et al. |
| 4,583,546 A | 4/1986 | Garde |
| 4,773,423 A | 9/1988 | Hakky |
| 4,784,267 A | 11/1988 | Gessler et al. |
| 4,832,198 A | 5/1989 | Alikhan |
| 4,917,694 A | 4/1990 | Jessup |
| 4,922,922 A | 5/1990 | Pollock et al. |
| 5,029,584 A | 7/1991 | Smith |
| 5,031,642 A | 7/1991 | Nosek |
| 5,048,683 A | 9/1991 | Westlake |
| 5,119,814 A | 6/1992 | Minnich |
| 5,132,087 A | 7/1992 | Manion et al. |
| 5,190,059 A | 3/1993 | Fabian et al. |
| 5,231,032 A | 7/1993 | Ludvigsen |
| 5,236,664 A * | 8/1993 | Ludvigsen ......... A61B 5/02042 204/416 |
| 5,285,682 A | 2/1994 | Micklish |
| 5,348,533 A | 9/1994 | Papillon et al. |
| 5,492,537 A | 2/1996 | Vancaillie |
| 5,522,805 A | 6/1996 | Vancaillie et al. |
| 5,629,498 A | 5/1997 | Pollock et al. |
| 5,633,166 A | 5/1997 | Westgard et al. |
| 5,650,596 A | 7/1997 | Morris et al. |
| 5,709,670 A | 1/1998 | Vancaillie et al. |
| 5,807,358 A | 9/1998 | Herweck et al. |
| 5,851,835 A | 12/1998 | Groner |
| 5,923,001 A | 7/1999 | Morris et al. |
| 5,931,824 A | 8/1999 | Stewart et al. |
| 5,944,668 A | 8/1999 | Vancaillie et al. |
| 5,956,130 A | 9/1999 | Vancaillie et al. |
| 5,984,893 A | 11/1999 | Ward |
| 6,006,119 A | 12/1999 | Soller et al. |
| 6,061,583 A | 5/2000 | Ishihara et al. |
| 6,359,683 B1 | 3/2002 | Berndt |
| 6,510,330 B1 | 1/2003 | Enejder |
| 6,699,231 B1 | 3/2004 | Sterman et al. |
| 6,728,561 B2 | 4/2004 | Smith et al. |
| 6,730,054 B2 | 5/2004 | Pierce et al. |
| 6,777,623 B2 | 8/2004 | Ballard |
| 7,001,366 B2 | 2/2006 | Ballard |
| 7,112,273 B2 | 9/2006 | Weigel et al. |
| 7,147,626 B2 | 12/2006 | Goodman et al. |
| 7,274,947 B2 | 9/2007 | Koo et al. |
| 7,364,545 B2 | 4/2008 | Klein |
| 7,384,399 B2 | 6/2008 | Ghajar |
| 7,430,047 B2 | 9/2008 | Budd et al. |
| 7,430,478 B2 | 9/2008 | Fletcher-Haynes et al. |
| 7,469,727 B2 | 12/2008 | Marshall |
| 7,499,581 B2 | 3/2009 | Tribble et al. |
| 7,641,612 B1 | 1/2010 | Mccall |
| D611,731 S | 3/2010 | Levine |
| 7,670,289 B1 | 3/2010 | Mccall |
| 7,703,674 B2 | 4/2010 | Stewart |
| 7,708,700 B2 | 5/2010 | Ghajar |
| 7,711,403 B2 | 5/2010 | Jay et al. |
| 7,749,217 B2 | 7/2010 | Podhajsky |
| 7,795,491 B2 | 9/2010 | Stewart et al. |
| 7,819,818 B2 | 10/2010 | Ghajar |
| 7,909,806 B2 | 3/2011 | Goodman et al. |
| 7,966,269 B2 | 6/2011 | Bauer et al. |
| 7,995,816 B2 | 8/2011 | Roger et al. |
| 8,025,173 B2 | 9/2011 | Michaels |
| 8,181,860 B2 | 5/2012 | Fleck et al. |
| 8,194,235 B2 | 6/2012 | Kosaka et al. |
| 8,241,238 B2 | 8/2012 | Hiruma et al. |
| 8,398,546 B2 | 3/2013 | Pacione et al. |
| 8,472,693 B2 | 6/2013 | Davis et al. |
| 8,576,076 B2 | 11/2013 | Morris et al. |
| 8,626,268 B2 | 1/2014 | Adler et al. |
| 8,693,753 B2 | 4/2014 | Nakamura |
| 8,704,178 B1 | 4/2014 | Pollock et al. |
| 8,792,693 B2 | 7/2014 | Satish et al. |
| 8,897,523 B2 | 11/2014 | Satish et al. |
| 8,983,167 B2 | 3/2015 | Satish et al. |
| 9,047,663 B2 | 6/2015 | Satish et al. |
| 9,171,368 B2 | 10/2015 | Satish et al. |
| 9,595,104 B2 | 3/2017 | Satish et al. |
| 9,646,375 B2 | 5/2017 | Satish et al. |
| 9,652,655 B2 | 5/2017 | Satish et al. |
| 9,936,906 B2 | 4/2018 | Satish et al. |
| 10,282,839 B2 | 5/2019 | Satish et al. |
| 2003/0095197 A1 | 5/2003 | Wheeler et al. |
| 2003/0130596 A1 | 7/2003 | Von Der Goltz |
| 2004/0031626 A1 | 2/2004 | Morris et al. |
| 2004/0129678 A1 | 7/2004 | Crowley et al. |
| 2005/0051466 A1 | 3/2005 | Carter et al. |
| 2005/0163354 A1 | 7/2005 | Ziegler |
| 2005/0265996 A1 | 12/2005 | Lentz |
| 2006/0058593 A1 | 3/2006 | Drinan et al. |
| 2006/0178578 A1 | 8/2006 | Tribble et al. |
| 2006/0224086 A1 | 10/2006 | Harty |
| 2007/0004959 A1 | 1/2007 | Carrier et al. |
| 2007/0108129 A1 | 5/2007 | Mori et al. |
| 2007/0243137 A1 | 10/2007 | Hainfeld |
| 2007/0287182 A1 | 12/2007 | Morris et al. |
| 2008/0029416 A1 | 2/2008 | Paxton |
| 2008/0030303 A1 | 2/2008 | Kobren et al. |
| 2008/0045845 A1 | 2/2008 | Pfeiffer et al. |
| 2008/0194906 A1 | 8/2008 | Mahony et al. |
| 2009/0076470 A1 | 3/2009 | Ryan |
| 2009/0310123 A1 | 12/2009 | Thomson |
| 2009/0317002 A1 | 12/2009 | Dein |
| 2010/0003714 A1 | 1/2010 | Bachur |
| 2010/0007727 A1 | 1/2010 | Torre-Bueno |
| 2010/0025336 A1 | 2/2010 | Carter et al. |
| 2010/0027868 A1 | 2/2010 | Kosaka et al. |
| 2010/0066996 A1 | 3/2010 | Kosaka et al. |
| 2010/0087770 A1 | 4/2010 | Bock |
| 2010/0150759 A1 | 6/2010 | Mazur et al. |
| 2010/0152563 A1 | 6/2010 | Turner et al. |
| 2010/0280117 A1 | 11/2010 | Patrick et al. |
| 2011/0066182 A1 | 3/2011 | Falus |
| 2011/0118647 A1 | 5/2011 | Paolini et al. |
| 2011/0192745 A1 | 8/2011 | Min |
| 2011/0196321 A1 | 8/2011 | Wudyka |
| 2011/0200239 A1 | 8/2011 | Levine et al. |
| 2011/0275957 A1 | 11/2011 | Bhandari |
| 2011/0305376 A1 | 12/2011 | Neff |
| 2011/0316973 A1 | 12/2011 | Miller et al. |
| 2012/0000297 A1 | 1/2012 | Hashizume et al. |
| 2012/0064132 A1 | 3/2012 | Aizawa et al. |
| 2012/0065482 A1 | 3/2012 | Robinson et al. |
| 2012/0210778 A1 | 8/2012 | Palmer et al. |
| 2012/0257188 A1 | 10/2012 | Yan et al. |
| 2012/0262704 A1 | 10/2012 | Zahniser et al. |
| 2012/0309636 A1 | 12/2012 | Gibbons et al. |
| 2012/0327365 A1 | 12/2012 | Makihira |
| 2012/0330117 A1 * | 12/2012 | Grudic ............ A61B 5/02028 600/324 |
| 2013/0010094 A1 * | 1/2013 | Satish ............ G06K 9/00 348/77 |
| 2013/0011042 A1 * | 1/2013 | Satish ............ G06K 9/00 382/134 |
| 2013/0094996 A1 | 4/2013 | Janssenswillen |
| 2013/0170729 A1 | 7/2013 | Wardlaw et al. |
| 2013/0301901 A1 | 11/2013 | Satish et al. |
| 2013/0303870 A1 * | 11/2013 | Satish ............ A61B 5/14535 600/371 |
| 2013/0308852 A1 | 11/2013 | Hamsici et al. |
| 2014/0079297 A1 | 3/2014 | Tadayon et al. |
| 2014/0207091 A1 | 7/2014 | Heagle et al. |
| 2014/0330094 A1 | 11/2014 | Pacione et al. |
| 2015/0046124 A1 * | 2/2015 | Bhavaraju ......... G01M 99/008 702/183 |
| 2015/0294460 A1 | 10/2015 | Satish et al. |
| 2016/0027173 A1 | 1/2016 | Satish et al. |
| 2017/0351894 A1 | 12/2017 | Satish et al. |

(56) References Cited

U.S. PATENT DOCUMENTS

| | | |
|---|---|---|
| 2017/0352152 A1 | 12/2017 | Satish et al. |
| 2019/0008427 A1 | 1/2019 | Satish et al. |

FOREIGN PATENT DOCUMENTS

| | | | |
|---|---|---|---|
| JP | S-59-161801 U | 10/1984 | |
| JP | S-62-144652 U | 6/1987 | |
| JP | H-06-510210 A | 11/1994 | |
| JP | H-11-37845 A | 2/1999 | |
| JP | 2002-331031 A | 11/2002 | |
| JP | 2003-075436 A | 3/2003 | |
| JP | 2005-052288 A | 3/2005 | |
| JP | 3701031 B2 | 9/2005 | |
| JP | 2006-280445 A | 10/2006 | |
| JP | 2008-055142 A | 3/2008 | |
| JP | 2011-036371 A | 2/2011 | |
| JP | 2011-515681 A | 5/2011 | |
| WO | WO-92/17787 A1 | 10/1992 | |
| WO | WO-1996/039927 A1 | 12/1996 | |
| WO | WO-2009/117652 A1 | 9/2009 | |
| WO | WO-2011/019576 A1 | 2/2011 | |
| WO | WO-2013/009709 A2 | 1/2013 | |
| WO | WO-2013/009709 A3 | 1/2013 | |
| WO | WO-2013/172874 A1 | 11/2013 | |
| WO | WO-2013/173356 A1 | 11/2013 | |
| WO | WO-2014/071399 A1 | 5/2014 | |
| WO | WO-2016/187070 A1 | 11/2016 | |

OTHER PUBLICATIONS

U.S. Appl. No. 15/943,561, filed Apr. 2, 2018, by Satish et al.
ACOG (2012). "Optimizing protocols in obstetrics," Series 2, 25 total pages.
Adkins, A.R. et al. (2014). "Accuracy of blood loss estimations among anesthesia providers," *AANA J.* 82(4):300-306.
Aklilu, A. Gauss Surgical Measures Blood Loss with a Smartphone. Jun. 14, 2012. <http://www.health2con.com/news/2012/06/14/gauss-surgical-measures-blood-loss-with-a-smartphone/>, 6 pages.
Al-Kadri, H.M. et al. (2014). "Effect of education and clinical assessment on the accuracy of post partum blood loss estimation," *BMC Preg. Childbirth* 14:110, 7 total pages.
AWHONN Practice Brief (2014). "Quantification of blood loss: AWHONN practice brief No. 1," *AWHONN* p. 1-3.
Bellad, M.B. et al. (2009). "Standardized Visual Estimation of Blood Loss during Vaginal Delivery with Its Correlation Hematocrit Changes—A Descriptive Study." South Asian Federation of Obstetrics and Gynecology 1:29-34.
Bose, P. et al. (2006). "Improving the accuracy of estimated blood loss at obstetric haemorrhage using clinical reconstructions," *BJOG* 113(8):919-924.
Eipe, N. et al. (2006). "Perioperative blood loss assessment—How accurate?" *Indian J. Anaesth.* 50(1):35-38.
Extended European Search Report dated Apr. 1, 2015, for EP Application No. 12 810 640.8, filed on Jul. 9, 2012, 8 pages.
Extended European Search Report dated Nov. 23, 2015, for EP Application No. 13 790 688.9, filed on May 14, 2013, 9 pages.
Extended European Search Report dated Nov. 17, 2015, for EP Application No. 13 790 449.6, filed on Jan. 10, 2013, 8 pages.
Extended European Search Report dated Nov. 4, 2016, for EP Application No. 16 183 350.4, filed on Jul. 9, 2012, 9 pages.
Final Office Action dated Feb. 1, 2016, for U.S. Appl. No. 14/072,632, filed Nov. 5, 2013, 24 pages.
Final Office Action dated Feb. 12, 2016, for U.S. Appl. No. 13/544,664, filed Jul. 9, 2012, 9 pages.
Final Office Action dated Aug. 26, 2016, for U.S. Appl. No. 13/894,054, filed May 14, 2013, 7 pages.
Final Office Action dated Jul. 26, 2016, for U.S. Appl. No. 14/876,628, filed Oct. 6, 2015, 5 pages.
Habak, P.J. et al. (2016). "A comparison of visual estimate versus calculated estimate of blood loss at vaginal delivery," *British J. Med. Medical Res.* 11(4):1-7.
Holmes, A.A. (2014). "Clinical evaluation of a novel system for monitoring surgical hemoglobin loss," *Anesth. Analg.* 119(3):588-594.
International Search Report dated Apr. 4, 2014, for PCT Application No. PCT/US2013/068576, filed on Nov. 5, 2013, 5 pages.
International Search Report dated Aug. 19, 2016, for PCT Application No. PCT/US2016/032560, filed on May 13, 2016, 2 pages.
International Search Report dated Sep. 17, 2012, for PCT Application No. PCT/US2012/045969, filed on Jul. 9, 2012, 2 pages.
International Search Report dated Sep. 24, 2013, for PCT Application No. PCT/US2013/040976, filed on May 14, 2013, 2 pages.
International Search Report dated Mar. 26, 2013, for PCT Application No. PCT/US2013/021075, filed on Jan. 10, 2013, 2 pages.
Jones, R. (2015). "Quantitative measurement of blood loss during delivery," *AWHONN* p. S41.
Kamiyoshihara, M. et al. (2008). "The Utility of an Autologous Blood Salvage System in Emergency Thoracotomy for a Hemothorax After Chest Trauma," *Gen. Thorac. Cardiovasc. Surg.* 56:222.
Lyndon, A. et al. (2010). "Blood loss: Clinical techniques for ongoing quantitative measurement," *CMQCC Obstetric Hemorrhage Toolkit*, pp. 1-7.
Lyndon, A. et al. (2015). "Cumulative quantitative assessment of blood loss," *CMQCC Obstetric Hemorrhage Toolkit Version 2.0*, pp. 80-85.
Manikandan, D. et al. (2015). "Measurement of blood loss during adenotonsillectomy in children and factors affecting it," *Case Reports in Clinical Medicine* 4:151-156.
Merck for Mother's Program (2012). Blood loss measurement: Technology opportunity assessment, 9 total pages.
Non-Final Office Action dated Aug. 4, 2015, for U.S. Appl. No. 14/072,632, filed Nov. 5, 2013, 21 pages.
Non-Final Office Action dated Aug. 13, 2015, for U.S. Appl. No. 13/544,664, filed Jul. 9, 2012, 8 pages.
Non-Final Office Action dated Aug. 2, 2016, for U.S. Appl. No. 13/544,664, filed Jul. 9, 2012, 6 pages.
Non-Final Office Action dated May 9, 2014, for U.S. Appl. No. 13/544,679, filed Jul. 9, 2012, 7 pages.
Non-Final Office Action dated Mar. 30, 2016, for U.S. Appl. No. 13/894,054, filed May 14, 2013, 9 pages.
Non-Final Office Action dated Sep. 5, 2014, for U.S. Appl. No. 13/738,919, filed Jan. 10, 2013, 8 pages.
Non-Final Office Action dated Mar. 20, 2015, for U.S. Appl. No. 14/613,807, filed Feb. 4, 2015, 8 pages.
Non-Final Office Action dated Dec. 15, 2015, for U.S. Appl. No. 14/876,628, filed Oct. 6, 2015, 8 pages.
Non-Final Office Action dated Apr. 20, 2017, for U.S. Appl. No. 13/894,054, filed May 14, 2013, 7 pages.
Notice of Allowance dated Feb. 17, 2015, for U.S. Appl. No. 14/072,625, filed Nov. 5, 2013, 10 pages.
Notice of Allowance dated Jul. 5, 2016, for U.S. Appl. No. 14/072,632, filed Nov. 5, 2013, 9 pages.
Notice of Allowance dated Oct. 19, 2016, for U.S. Appl. No. 14/072,632, filed Nov. 5, 2013, 9 pages.
Notice of Allowance dated May 12, 2014, for U.S. Appl. No. 13/544,646, filed Jul. 9, 2012, 10 pages.
Notice of Allowance dated Sep. 3, 2014, for U.S. Appl. No. 13/544,679, filed Jul. 9, 2012, 8 pages.
Notice of Allowance dated Nov. 10, 2014, for U.S. Appl. No. 13/738,919, filed Jan. 10, 2013, 10 pages.
Notice of Allowance dated Jun. 25, 2015, for U.S. Appl. No. 14/613,807, filed Feb. 4, 2015, 10 pages.
Notice of Allowance dated Oct. 26, 2016, for U.S. Appl. No. 14/876,628, filed Oct. 6, 2015, 11 pages.
Notice of Allowance dated Feb. 15, 2017, for U.S. Appl. No. 13/544,664, filed Jul. 9, 2012, 10 pages.
Pogorelc, D. (Jun. 6, 2012). "iPads in the OR: New Mobile Platform to Monitor Blood Loss During Surgery," MedCityNews, located at http://medcitynews.com/2012/06/ipads-in-the-or-new-mobile-platform-to-monitor-blood-loss-during-surgery, 4 pages.
Roston, A.B. et al. (2012). "Chapter 9: Blood loss: Accuracy of visual estimation," in *A comprehensive textbook of postpartum hemorrhage: An essential clinical reference for effective management*, $2^{nd}$ edition, Sapiens publishing, pp. 71-72.

(56) References Cited

OTHER PUBLICATIONS

Sant et al. (2012). "Exsanguinated Blood Volume Estimation Using Fractal Analysis of Digital Images," *Journal of Forensic Sciences* 57:610-617.

Schorn, M.N. (2010). "Measurement of blood loss: Review of the literature," *J. Midwifery and Women's Health* 55(1):20-27.

Sukprasert, M. et al. (2006). "Increase accuracy of visual estimation of blood loss from education programme," *J. Med. Assoc. Thai* 89(suppl. 4):S54-S59.

Written Opinion of the International Searching Authority dated Apr. 4, 2014, for PCT Application No. PCT/US2013/068576, filed on Nov. 5, 2013, 6 pages.

Written Opinion of the International Searching Authority dated Aug. 19, 2016, for PCT Application No. PCT/US2016/032560, filed on May 13, 2016, 6 pages.

Written Opinion of the International Searching Authority dated Sep. 17, 2012, for PCT Application No. PCT/US2012/045969, filed on Jul. 9, 2012, 4 pages.

Written Opinion of the International Searching Authority dated Sep. 24, 2013, for PCT Application No. PCT/US2013/040976, filed on May 14, 2013, 4 pages.

Written Opinion of the International Searching Authority dated Mar. 26, 2013, for PCT Application No. PCT/US2013/021075, filed on Jan. 10, 2013, 6 pages.

U.S. Appl. No. 15/416,986, filed Jan. 26, 2017, by Satish et al.

U.S. Appl. No. 15/594,017, filed May 12, 2017, by Satish et al.

Non-Final Office Action dated Feb. 21, 2019, for U.S. Appl. No. 15/594,017, filed May 12, 2017, 23 pages.

Notice of Allowance dated Nov. 20, 2017, for U.S. Appl. No. 13/894,054, filed May 14, 2013, 8 pages.

Notice of Allowance dated Jan. 24, 2019, for U.S. Appl. No. 15/416,986, filed Jan. 26, 2017, 8 pages.

\* cited by examiner

METHOD FOR PROJECTING BLOOD LOSS OF A PATIENT DURING A SURGERY

CROSS-REFERENCE TO RELATED APPLICATIONS

This application claims the benefit of U.S. Provisional Application No. 62/162,128, filed on May 15, 2015, which is incorporated by reference in its entirety.

TECHNICAL FIELD

This invention relates generally to the field of blood loss, and more specifically to new and useful systems and methods for tracking patient blood loss and/or managing patient fluid status.

SUMMARY

Systems for monitoring blood loss include a display for simultaneously depicting a current blood loss metric at different time points or along a time line. In addition, historical or reference blood loss information is provided on the display so that the healthcare provider can compare the current blood loss to other metrics, so that the healthcare provider can more accurately assess and manage the patient's status and alternatively be provided with other clinical outcome data to better understand clinical implications of the current surgical procedure.

In one embodiment, a method of patient monitoring is provided, comprising displaying an estimate of real-time blood loss value for a patient corresponding to a first time point of a current surgical procedure, displaying an updated estimate of real-time blood loss value for the patient corresponding to a second time point after the first time point, and displaying at least one reference blood loss value corresponding to the first time point, the second time point, or a third time point after the second time point. The set of reference blood loss values may be provided by selecting at least one data set from a database of prior surgical procedures. The estimate of blood loss and the updated estimate of blood loss may be displayed simultaneously on a monitor screen. The estimate of blood loss and the updated estimate of real-time blood loss may be provided on a two-dimensional plot. The two-dimensional plot may depict estimated blood loss over time. The set of reference blood loss values may be provided on the two-dimensional plot. Displaying the set of reference blood loss values may comprise displaying at least one blood loss tracing over time. Each of the at least one blood loss tracings may be based upon a single historical surgical procedure. Displaying the set of reference blood loss values may comprise displaying a plurality of database blood loss tracings over time. The set of reference blood loss values may be provided as at least one band plot on the two-dimensional plot. The at least one band plot may comprise a plurality of nested confidence bands on the two-dimensional plot. The estimate of real-time blood loss and updated estimate of blood loss may be overlaid on the set of comparative blood loss values. The method may further comprise receiving the set of reference blood loss values from a remote server. The method may further comprise selecting the set of reference blood loss values based upon the surgical procedure. The method may further comprise selecting the set of reference blood loss values based upon one or more patient factors. The method may further comprise selecting the set of reference blood loss values based upon one or more health condition or disease factors, or practice-based factors. The set of reference blood loss values are an average, median, mode or a range of historical blood loss values from a plurality of prior surgical procedures. Each of the plurality of prior surgical procedures may be the same type as the current surgical procedure. The plurality of prior surgical procedures may be surgical procedures selected based upon the N closest blood loss tracings based upon a curve-of-best-fit to a current blood loss tracing that includes the estimate of blood loss and the updated estimate of blood loss. N may be between 1 and 50, or between 1 and 10. The method may further comprise comparing the updated estimate of blood loss value to a threshold value, and displaying a message, different from the estimate of real-time blood loss, the updated estimate of blood loss and the set of comparative blood loss values, if the threshold value is met or exceeded. The threshold value may be a time-dependent threshold value. The threshold value may be determined by the set of reference blood loss values. The message may be a clinical message indicating that a blood transfusion threshold has been met, or that a blood transfusion threshold is estimated to be met at a future time point. The at least one reference blood loss value may be at least one predicted future blood loss value corresponding to a third time point. The at least one predicted future blood loss value may comprise providing at least two predicted future blood loss values, wherein one of the least two predicted future blood loss values is a lower limited predicted future blood loss value at the third time point. Displaying at least one reference blood loss value corresponding to the first time point may comprise displaying at least one predicted future blood loss tracing that includes the at least one predicted future blood loss value at the third time point. Displaying at least one predicted future blood loss value may comprise displaying a predicted future blood loss area plot that includes the at least one predicted future blood loss value at the third time point. The predicted future blood loss area plot may be bound by the updated estimate of blood loss value at the second time point.

In another embodiment, a patient monitoring system is provided, comprising a camera configured to generate blood loss images from a surgical procedure, and one or more processors configured to display updated estimated blood loss information for at least two time points on an information display, wherein the estimated blood loss information is generated from the blood loss images, and to display reference blood loss information on the information display, wherein the reference blood loss information comprises a plurality of blood loss values over different time points of at least one different surgical procedure. The patient monitoring system may further comprise a display, provided in a housing with the camera. The one or more processors may be further configured to select the plurality of blood loss values over different time points of at least one different surgical procedure from a database of prior surgical procedures. The one or more processors may be configured to simultaneously display the updated estimated blood loss information and the reference blood loss information on a monitor screen. The updated estimated blood loss information and the reference blood loss information may be provided on a two-dimensional plot, and may depict estimated blood loss over time. The reference blood loss information may be at least one blood loss tracing over time. The updated estimated blood loss information and the reference blood loss information are overlaid on a graph. At least one of the one or more processors may be provided on a remote server separate from the camera. The one or more processors may be further configured to select the plurality of blood loss values over different time points by filtering with one or more patient factors. The one or more processors may be further configured to select the plurality of blood loss values over different time points by further filtering with one or more health condition or disease factors, or practice-based factors. The one or more processors may be further configured to compare the updated estimate of blood loss value to a threshold value, and display a message, different from the estimate of real-time blood loss, the updated estimate of blood loss and the set of comparative blood loss values, if the threshold value is met or exceeded. The message may be a clinical message indicating that a blood transfusion threshold has been met, or a clinical message indicating that a blood transfusion threshold is estimated to be met at a future time point. The reference blood loss information may be at least one predicted future blood loss value corresponding to a third time point. The at least one predicted future blood loss value may comprise providing at least two predicted future blood loss values, wherein one of the least two predicted future blood loss values is a lower limited predicted future blood loss value at the third time point. The display of at least one reference blood loss value corresponding to the first time point may comprise the display of at least one predicted future blood loss tracing that includes the at least one predicted future blood loss value at the third time point. Displaying at least one predicted future blood loss value may comprise displaying a predicted future blood loss area plot that includes the at least one predicted future blood loss value at the third time point. The predicted future blood loss area plot may be bound by the updated estimate of blood loss value at the second time point.

DESCRIPTION OF THE EMBODIMENTS

Figure 1A:
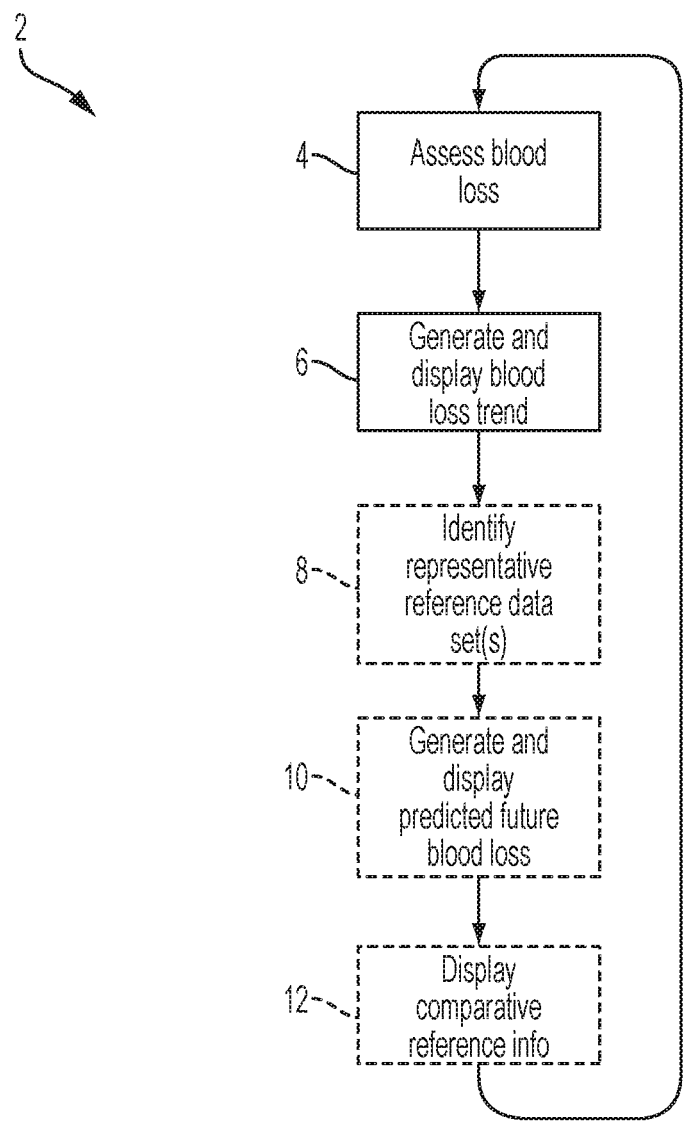
FIG. 1A is a flowchart representation of a method.
Figure 1B:
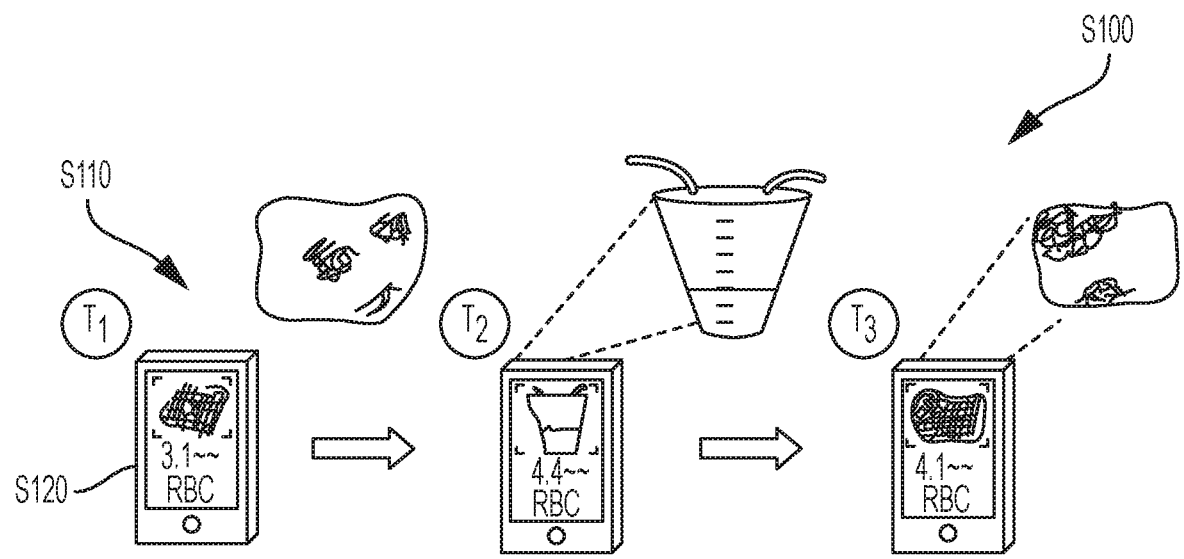
FIG. 1B is a schematic illustration of a step of the flowchart in FIG. 1A.

The following description of the embodiments of the invention is not intended to limit the invention to these embodiments but rather to enable a person skilled in the art to make and use this invention.

Accurate estimation of blood loss during surgical procedures is an important factor in assessing the fluid status and either avoiding unnecessary blood transfusion, or avoiding delays in blood transfusion that may place patient safety at risk. The estimation of blood loss has traditionally relied upon visual estimation by the surgeon and anesthesiologist, but studies have shown that visual estimation is highly inaccurate, with significant underestimation of higher levels of blood loss, and overestimation of lower levels of blood loss. The accuracy is also impacted by the dilution from other non-blood fluids in the surgical field, including the use of intravenous fluids to irrigate and clean the operative field, as well as patient fluids, such as amniotic fluids, and also impacted by lighting conditions in the operating room.

The use of computing imaging systems in the operating room to perform quantitative estimates of blood loss has been shown to be substantially more accurate provider-based visual estimation. In addition to more accurate intra-operative blood loss estimation, the availability of multiple accurate blood loss estimates in associated with time information for each estimate provides blood loss trend information, which can provide additional clinical insights and information than the individual blood loss estimates alone. Quantitative systems may facilitate or automate the collection of blood loss information, which can be stored in a blood loss information database, along with other health information related to the specific procedure or surgery. The blood loss trend information from a completed procedure, in conjunction with other patient, disease or health condition, surgery and/or practice-based factors or information from the patient's health care records, may provide valuable clinical insights that can improve future clinical outcomes and patient safety, and facilitate changes to clinical practice guidelines.

For example, the blood trend information from a completed surgery or procedure may be associated with patient characteristics (e.g., age, gender, height, weight, family history, surgical history, cardiac history, history of hemophilia/platelet disorders, metabolic equivalent status, pre-operative platelet count, pre-operative hematocrit, pre-operative hemoglobin, history of autoimmune disorder, anti-coagulant use), health condition or disease characteristics (e.g., pregnancy history, cancer stage, cancer grade), treatment and/or surgery information (e.g., fibroidectomy, hysterectomy, liver resection, coronary bypass) and practice-based factors (e.g., selected prior procedures limited to the surgeon's or anesthesiologist's prior procedures, practice group's prior procedures, practitioner experience level, number of prior procedures, insurer's practitioners, practitioner geographic location, residency training or board specialty (e.g. family practice, OB/GYN), and combinations thereof. Information from the selected reference information of prior procedures may be provided simultaneously on a display of the current blood loss information in a text and/or graphical manner, to provide further context to the current blood loss information so that the practitioner can better identify potential clinical issues and/or risks during the course of the procedure or surgery. The selected reference information may be presented on the display as blood loss information from one or more separate or individual procedures, and/or may be displayed as aggregate information from two or more procedures, and/or clinical practice guideline or model procedures not based upon actual or specific prior procedures.

In addition to provide useful comparative reference information based upon prior procedures, prior blood loss information data sets may also be used to predict and/or provide future blood loss trend information, either based upon pre-operative factors as listed above, which may also be updated during the surgery based upon actual quantitative blood loss estimates during the surgery. For example, one or more blood loss data sets from the procedure database may be provided on the display, so that the healthcare provider can be provided with a range of blood loss trends that may be expected in the current surgery, based upon one or more factors listed above used to select the data sets. In some embodiments, because of the wide variation in blood loss trends, even after applying one or more selection factors, a matching process may be applied to further select or limit the data sets selected from the procedure database, which may provide more relevant or useful information to the healthcare provider. For example, parametric or non-parametric selection algorithms may be used, such as a curve-of-best-fit or a k-nearest neighbor algorithm, to select the reference datasets most similar to the surgery. Then, during the surgery, as initial blood loss trend information is obtained, the selection of reference data sets may be further refined or changed. Using the selected data sets, a predicted blood loss trend may be generated and displayed for the expected remainder of the procedure, which can be updated as additional measured blood loss information is obtained. The same data sets may be used to determine a predicted upper limit and/or a predicted lower limit of blood loss over the future time frame. In addition to the blood loss information, the selected data sets may also contain other information, such as if or when a blood transfusion occurred, and/or the rate(s) and/or types of intravenous fluid infused, occurrences of hypovolemic shock, hypotensive events. The information on the risk or rate of such events may also include time information, and displayed on a time line along with the current and reference blood loss information.

Generally, the systems and methods described herein for assessing fluids from a patient are used to assess fluids that are lost by a patient during a surgical procedure. Images of the fluids may be intermittently generated and evaluated in order to assess the fluids. For example, the systems and methods described herein may be used to track or otherwise estimate, based at least in part on the images of fluid, a quantity of fluid (e.g., blood) lost by the patient during the surgical procedure and/or quantity of a blood component (e.g., hemoglobin). In other examples, the systems and methods may additionally or alternatively be used to track or otherwise assess total mass, total volume, and/or aggregate concentration of red blood cells, platelets, plasma, and/or other blood components lost by the patient during the surgical procedure. These assessments, and other fluid-related information described in further detail below, may be updated and displayed in substantially real-time during the surgical procedure and/or at the conclusion of the surgical procedure.

The system may be used in conjunction with one or more displays, and each display may provide the same or different information. For example, the anesthesiologist or anesthetist may be provided with a separate display with different information than the display used by the surgeon or surgical nursing staff. In some variations, the system may accept information input from other monitoring systems, e.g. blood pressure, heart rate, respiratory rate, or may be configured to output information or display signals to other general or proprietary systems or displays. The system may comprise one or more processors, one or more memory banks, and one or more I/O interfaces, and one or more optical input devices, such as an optical scanner or camera, for detecting the blood content of one or more blood retention or containing structures, as described in greater detail below. In some variations, the optical input devices may also be used to input or control the system, using gesture recognition or other methods of optical input. The system is further configured with image processing hardware and/or software to extract the blood information from the blood retention or containing structures. Other input devices, such as a foot pedal, mouse, or wand, may also be provided. Exemplary hardware and software components for the system are described in U.S. Pat. Nos. 8,792,693, 8,983,167, and U.S. Patent Publication No. 2015/0294461, which are each hereby incorporated by reference in their entirety.

For example, the evaluation of the images may include estimating a blood component concentration. The blood component may be red blood cells (e.g., by volume) or hemoglobin, but may additionally or alternatively include other suitable components of blood. The estimation of blood component concentration may be based on various template matching techniques and/or parametric modeling techniques, as described below.

For instance, to convert pixel color values in the receptacle image region to a blood component concentration, template matching techniques may include comparing a redness intensity of the receptacle image region against redness intensity from template images (e.g., a training set, samples analyzed previously). Each template image may be contained within a library of template images, and may be associated with a known blood, hemoglobin, red blood cell mass or volume, and/or other fluid characteristics. Generally, where the redness intensity of the receptacle image region is substantially similar to (and is paired with) a closest-matching template image, the receptacle image region may be estimated as depicting the same blood component concentration as the closest-matching template image.

In one example, K-nearest neighbor methods may be used for the template matching. More specifically, a K-nearest neighbor method may be used to compare the redness intensity of the receptacle image region with redness intensity values in the template images. Additionally or alternatively, a K-nearest neighbor method may be used to compare greenness intensity and/or a blueness intensity (e.g., in conjunction with a redness intensity) of pixels in the receptacle image region with greenness and/or blueness intensity values of the template images. Thus, the receptacle image region may be paired with the closest-matching template image identified with the K-nearest neighbor method, and the receptacle image region may be estimated as depicting the same blood component concentration associated with the closest-matching template image.

In another example, absolute differences in pixel intensities (e.g., in red, green, and/or blue intensities or color values) may be used for the template matching. Such an absolute difference in pixel intensities may be calculated at a wavelength of light that correlates with the blood component (e.g., at about 400 nm for estimating hemoglobin concentration). More specifically, a sum of absolute differences in pixel intensities may be used to compare pixel intensities between the receptacle image region and each template image. The closest-matching template image is identified when the sum of absolute differences is substantially minimal compared to other sums of absolute differences calculated for the receptacle image region and other template images. Thus, the receptacle image region may be paired with the closest-matching template image identified with the sum of absolute differences method, and the receptacle image region may be estimated as depicting the same blood component concentration associated with the closest-matching template image.

Additionally, parametric models may be used to convert pixel color values in the receptacle image region to a blood component concentration. Generally, color values of the template images may be used to train or generate a parametric model (mathematical function, curve, or algorithm etc.) that correlates a pixel color value to a blood component concentration. The parametric model may take an input of pixel intensities or color values (e.g., from the receptacle image region) and converted it into an output of estimated blood component concentration value.

The image processing component(s) may be provided in the same or different housing or location as the optical input device(s) and/or display(s). In some variations, the images or video from the optical input devices may be transmitted to a remote server for processing and the extracted blood loss information is transmitted back to the local processor(s) for display. Likewise, the database with the reference data sets may also be contained in the same or different housing, or provided on a remote server, and selection instructions may be provided and the data sets may be selected and/or processed by the remote server and transmitted back to the local processor(s).

1. Method

In one embodiment, depicted in FIG. 1A, the method 2 of assessing blood loss and displaying blood loss trend information, and optional comparative or reference information is provided. The method 2 involves the iterative quantitative estimation or assessment 4 of incremental or cumulative blood loss at a time point or over a time period, as disclosed, for example, in U.S. Pat. Nos. 8,792,693, 8,983,167, and U.S. Patent Publication No. 2015/0294461. The iterative assessment of blood loss over time permits the generation and display 6 of a blood loss trend. The blood loss trend may comprise, a text or graphical indicator of the rate of blood loss over time, and may be quantitative, such as a 2D time graph or tracing of blood loss (y-axis) over time (x-axis), or qualitative, such as a red/yellow/green indicators, and may reflect an absolute value of blood loss trend or a relative value of blood loss trend, compared to a reference standard or reference blood loss data set.

The method 2 may optionally comprise a database search and identification 8 of one or more representative data sets, based optionally upon the one or more exemplary patient, health condition or disease state, treatment or practice-based factors previously described. One or more factors may be optionally weighted to select the desired data set(s).

The selected data set(s) may be further analyzed and processed to provide one or more predictions of future blood loss 10, based upon pre-operative factors described above, and optionally during the surgery, based upon one or more time points or time segments of the current blood loss trend. For example, at the start of a surgical procedure, a representative maximum and/or minimum blood loss trend may be displayed, based upon one or more factors or characteristics previously described. As the surgical procedure progresses and a current blood loss trend is generated, the selected data set(s) may be further sub selected or re-selected based upon one or more data points or ranges of the current blood loss trend to provide a predicted future trend. This may be depicted as an upper and/or lower limit extrapolated from the current blood loss value on a 2D graph, and may be in the form of tracings, or an area/band plot, for example. The area/band plot may have a generally conical or otherwise widening shape from the current blood loss value and time point, toward the later future time points.

In other examples, one or more selected comparative data set(s) may be directly provided on the display 12 on a graph, either simultaneously with the current blood loss trend, or alternating on the display in an automated fashion or as selected by the user. Further details of the method are provided below.

Figure 1C:
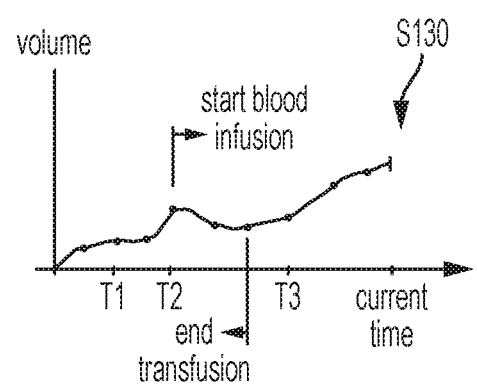
FIG. 1C is a schematic illustration of a step of the flowchart in FIG. 1A.
Figure 1D:
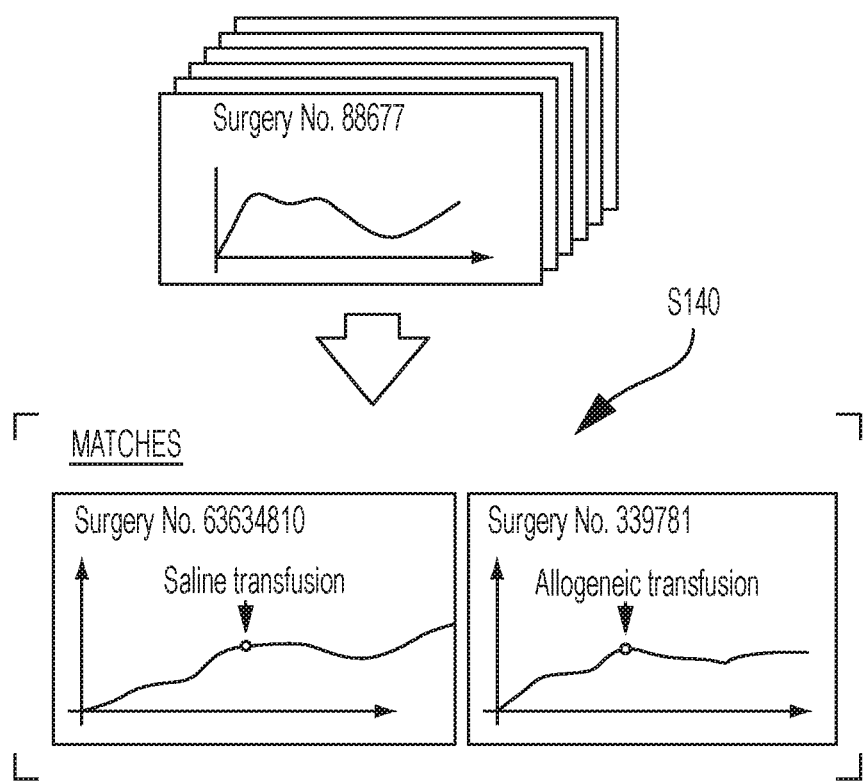
FIG. 1D is a schematic illustration of a step of the flowchart in FIG. 1A.
Figure 1E:
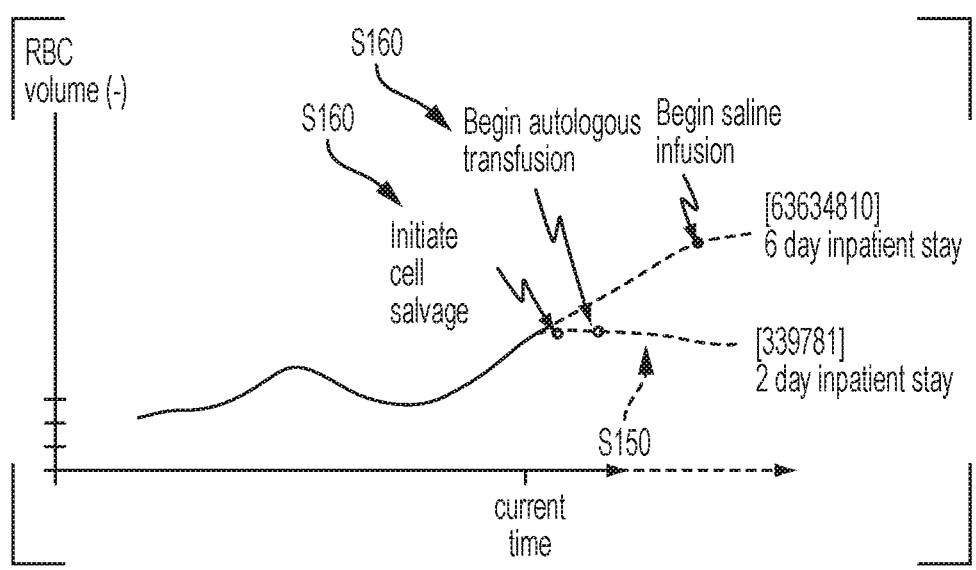
FIG. 1E is a schematic illustration of a step of the flowchart in FIG. 1A.

As shown in FIGS. 1B to 1E, a method S100 for projecting blood loss of a patient during a surgery includes: collecting a series of digital photographic images of a set of bloodied containers or blood retention structures during the surgery in Block S110; for each bloodied container in the set of bloodied containers, estimating a quantity of a blood component in a bloodied container based on color values of pixels in the corresponding digital photographic image of the bloodied container in Block S120; rendering a plot of blood component loss by the patient within a user interface based on blood component quantity estimates for the set bloodied containers in Block S130 of FIG. 1C; matching the plot of blood component loss by the patient with an historic blood component loss period of a reference surgery in Block S140 of FIG. 1D; extending the plot of blood component loss by the patient in the user interface into a future time with blood component loss data from the reference surgery in Block S150 of FIG. 1E; and rendering markers for an action and an event occurring during the reference surgery with the plot of blood component loss by the patient in the user interface in Block S160.

2. Applications

As noted previously, generally, the method S100 can be implemented by a local computing device or by a remote computer system to merge real-time patient blood loss data during a surgery with historic blood loss data from reference surgeries to predict future blood loss of the patient and to identify actions that may positively or negatively impact patient blood loss and the overall success of the procedure. The blood loss data for a current operation can thus be shown with a future blood projection extracted from blood loss data of a similar past surgery or group of surgeries, as well as with relevant actions and projected outcome data for the surgery based on results of the past surgery. In particular, the method S100 can be executed locally or remotely during a surgery: to extract blood component loss information from images of various blood containers or blood retention structures, such as one or more surgical suction canisters and one or more surgical textiles (e.g., surgical gauze sponges, surgical dressings, surgical towels); to aggregate blood component loss data for the patient into total changes in the patient's circulatory system throughout the surgery; to match changes in the patient's circulatory system during the surgery to circulatory changes occurring in patients during reference surgeries; to forecast future changes in the patient's circulatory system and the effect of various actions on the patient's circulatory system during the surgery based on data from the matched reference surgeries (e.g., rather than based solely on a trajectory or slope of current changes in the patient's circulatory system); and to present these forecast and action data to a user (e.g., a nurse, surgeon, anesthesiologist) in real-time during the surgery, such as by rendering these data on a tablet or on a standalone digital display arranged within the operating room.

One or more blocks of the method S100 can be executed by a cloud-based computer system, a mainframe computer system, a grid-computer system, or any other suitable computer system. In one implementation, Blocks of the method S100 are implemented by a handheld (e.g., mobile) computing device, such as by a smartphone or tablet computer executing a native blood component analysis application and installed within an operating room or other surgical setting. In this implementation, a camera integrated into the computing device captures images of a bloodied surgical suction canister and/or bloodied surgical textiles (hereinafter "bloodied containers"), and a processor integrated into the computing device executes Blocks S110 and S120 of the method S100 to transform these images into blood component concentration values, fluid volume values, and/or blood component amounts (e.g., masses, volumes) in each bloodied container. Additionally or alternatively, the computing device can communicate with a remote server, such as over the Internet via a wireless connection, and the remote server can perform various Blocks of the method S100—including accessing a remote database of blood component loss data from reference surgeries—before transmitting blood component loss plots, blood component loss projections, surgical action markers, and surgical event markers back to the computing device for visual and/or audible presentation to a user. For example, the local computing device can also include or can be coupled to a digital display and can render a user interface—including blood component loss plots, blood component loss projections, surgical action markers, and/or surgical event markers—for review by a user throughout the surgery. Alternatively, Blocks of the method S100 can be executed by a standalone blood management system, such as a standalone blood management system including a surgical suction canister stand, a camera, a camera stand supporting the camera adjacent the surgical suction canister, a digital display, local memory, and/or a processor executing various Blocks of the method S100.

The method S100 is described generally for tracking and projecting future loss of red bloods cells (RBCs) by a patient. However, the method S100 can additionally or alternatively track and project loss of whole blood, hemoglobin, platelets, plasma, and/or other components of blood. Furthermore, the method S100 is described generally as matching RBC loss by the patient to RBC losses in reference surgeries to project future RBC loss by the patient. However, as described below, the method S100 can additionally or alternatively track and project the patient's total estimated blood loss ("EBL"), deviation from euvolemia, and/or changes in the patient's intracirculatory hematocrit, etc.

3. Image Processing

Block S110 of the method S100 recites collecting a series of digital photographic images of a set of bloodied containers during the surgery; and Block S120 of the method S100 recites, for each bloodied container in the set of bloodied containers, estimating a quantity of a blood component in a bloodied container based on color values of pixels in the corresponding digital photographic image of the bloodied container. Generally, a local or remote computer system executing Block S110 and S120 of the method S100 can implement methods and techniques described in U.S. Pat. Nos. 8,792,693 and 8,983,167, which are each incorporated in their entirety by this reference, to capture and transform images of surgical textiles and surgical suction canisters, respectively, into RBC content (e.g., mass, volume) estimates. For example, in Block S120, a computer system can collect an image of a surgical textile from an integrated or external camera and can then implement template matching techniques to match a portion the image corresponding to the surgical textile to a template image of a surgical textile of known RBC content. Similarly, in Block S120, the computer system can implement template matching techniques to match a color of a pixel cluster in a portion of an image corresponding to a surgical suction canister to a template color corresponding to known RBC concentration, and the computer system can then implement edge detection techniques to identify the fluid level in the canister, transform this fluid level into a fluid volume, and then combine this fluid volume with the RBC concentration to estimate the RBC content of the canister. Alternatively, the computer system can apply parametric models to images of surgical textiles and/or to images of surgical suction canisters to transform color values of pixels or pixel clusters in such images into RBC content and/or concentration values.

In Block S120, the computer system can store both the RBC content estimate and a time of the blood component content estimate (e.g. $T_1, T_2, T_3$ shown in FIG. 1B) in local or remote memory. For example, the computer system can tag an RBC content estimate with a time that an image of the corresponding bloodied container was captured. The computer system can also tag the blood component content estimate with a type a the bloodied container, such as with a "suction canister," "surgical towel," "surgical sponge," or "surgical drape" tag.

4. Patient RBC Loss Plot

Block S130 of the method S100 recites rendering a plot of blood component loss by the patient within a user interface based on blood component quantity estimates for the set bloodied containers. Generally, in Block S 130, the computer system aggregates RBC content estimates calculated from a series of images of various bloodied containers captured during the surgery (i.e., "discrete Blood loss events") and generates a digital plot (e.g., two-dimensional plot) of patient RBC loss during the surgery from these discrete Blood loss events. In particular, the computer system sum total RBC counts from blooded surgical textiles and can update an RBC count for a surgical suction canister as the canister fills will fluid and is reimages throughout the surgery to calculate total RBC to maintain a current estimate of total RBC loss by the patient.

The computer system can update the total patient RBC loss estimate in response to generation of a RBC content estimate from each subsequent image of a bloodied canister captured during the surgery (i.e., "blood loss event"). The computer system can store each new total patient RBC loss with a time of the corresponding blood loss event and then generate a point cloud of total patient RBC loss during the surgery up to the current time, wherein each point in the point cloud defines a total estimated patient RBC loss at a particular time (e.g. $T_1$, $T_2$, and $T_3$ shown in FIG. 1C). (The computer system can additionally or alternatively collect patient RBC loss data entered manually by a user, by interfacing with volume and/or fluid quality sensors integrated into a surgical textile cell salvage centrifuge, and/or by interfacing with volume and/or fluid quality sensors integrated into a surgical suction canister.)

In one implementation, the computer system also accounts for intravenous RBC infusions into the patient during the surgery. In particular the computer system can track volumes or masses RBCs infused back into the patient and subtract these masses or volumes of RBCs from the total estimated patient RBC loss. In one example, a user (e.g., a nurse, an anesthesiologist) enters infusion information—such as infusion rate, infusion start time, and total infusion volume—for an allogeneic blood transfusion in the user interface. In this example, the computer system combines these infusion data with a default hematocrit (Ht) (e.g., 42.5%) for the infusion volume, reads a Ht value from a barcode or other symbol(s) on a blood infusion bag containing the infusion volume, or prompts the user to enter a result of a Ht spin down test of a sample from the infusion volume. In another example, the computer system prompts the user to enter into the user interface a volume or mass of salvaged RBCs and a volume of saline (or plasma, etc.)

mixed with the salvaged RBCs prior to infusion back into the patient and calculate a Ht of the infusion volume accordingly. In this example, the computer system can also prompt the user to enter a start time and an infusion rate of the salvaged RBCs; alternatively, the computer system can sample a flow sensor coupled to an infusion bag to determine a flow rate of the infusion.

The computer system can then combine the flow rate, Ht, infusion start time, total fluid volume, and/or total RBC mass or volume for the infusion to track a mass or volume of RBCs infused into the patient's circulatory system over time and can subtract a mass of volume of infused RBCs from RBC estimates for sequential Blood loss events to calculate a total RBC loss for the patient. For example, during an infusion of a volume containing RBCs, the computer system can: integrate the infusion rate over a period of time between a preceding Blood loss event and a new Blood loss event to estimate the infused volume for the period of time; transform the infused volume into a RBC volume for the period of time based on the Ht of the infused volume; and subtract the RBC volume from new the blood loss event to calculate a total RBC loss for the patient up to the current time.

When generating a plot of RBC In Block S130, the computer system can also shift a discrete blood loss events in time to compensate for lag between collection of blood in the corresponding container and estimation of the corresponding image to estimate the RBC content of the corresponding container. In one implementation, the computer system can apply a static default lag for particular types of bloodied containers. For example, an average delay of two minutes may occur between initial use of a surgical textile to collect blood from within or around a patient processing of an image of the surgical textile to estimate its RBC content; the computer system can therefore compensate for this delay by shifting blood loss events for surgical textiles back in time by two minutes from the time a corresponding image is processed. Alternatively, the computer system can apply a dynamic lag time for each type of bloodied container, such as based on: historical lags times for a type of the current surgery; a lag time history of a surgeon, nurse, and/or anesthesiologist on duty in the operating room; etc. Yet alternatively, the computer system can prompt a user to enter lag time for each bloodied container imaged during a surgery and then apply these manual lag estimates to each corresponding blood loss event to generate a plot of patient RBC loss.

Figure 3A:
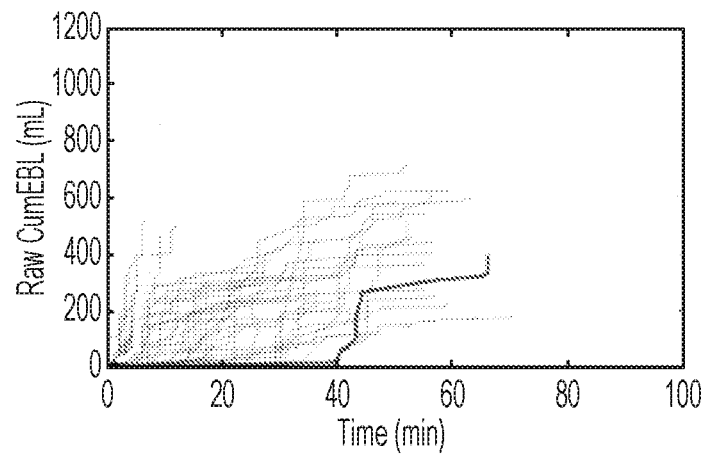
FIGS. 3A and 3B are a flowchart representation of one variation of the method, before and after smoothing, respectively
Figure 3B:
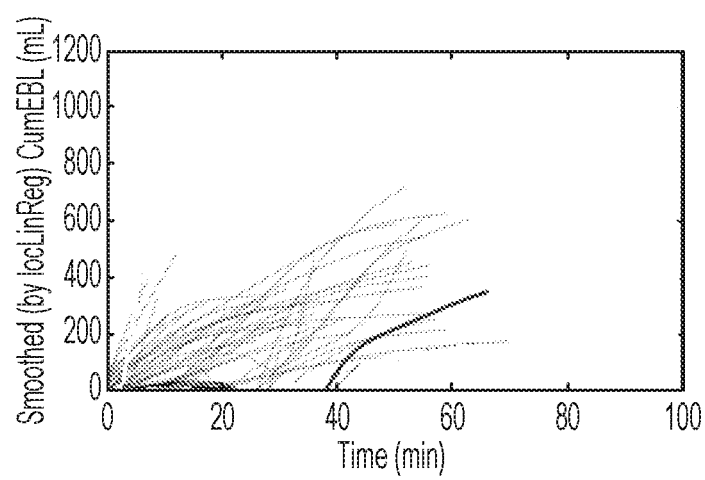

In Block S130, the computer system can therefore plot total estimated RBC change in the patient's circulatory system by summing RBC losses and additions for each blood loss event during the surgery. The computer system can also interpolate blood loss values between adjacent points in the RBC loss plot to generate a smooth (e.g., contiguous) RBC loss curve, as shown in FIGS. 3A and 3B, for example. The computer system can smooth the raw RBC loss plot in FIG. 3A by applying a moving average, locally weighted linear regression, spline smoothing, a Kalman filter, a Gaussian kernel, or any other smoothing method technique, to generate the smoothed or processed RBC loss plot depicted in FIG. 3B.

4. Matching

Block S140 of the method S100 recites matching the plot of blood component loss by the patient with an historic blood component loss period of a reference surgery. Generally, the computer system can execute Block S140 to match the trajectory of the patient's RBC loss to a trajectory of RBC loss by a patient in a reference surgery of known outcome. In particular, the computing device accesses a database of historic RBC loss periods generated as described above during historic surgeries (or "reference surgeries") and compares these reference surgeries to all or a portion of the current patient RBC loss plot to identify one or a limited number of similar historic blood loss periods. For example, in Block S140, the computer system can compare the whole RBC loss plot of the current surgery to whole reference surgeries stored in a surgical database. Alternatively, the computer system can compare only a portion of the reference surgery of the current surgery, such as the previous five minutes of the current surgery, to sections of reference surgeries of similar length stored in the surgical database.

In one implementation, the computer system executes template matching techniques to match the current patient RBC loss plot to a reference surgery. In this implementation, the computer system can translate a segment (e.g., the most-recent five minutes) of the current patient RBC loss plot into a virtual image on a standard time and RBC volume (or mass) scale. The computer system can then execute template matching techniques to identify a portion of a virtual image of a reference surgery that substantially matches the virtual image of the segment of the current RBC loss plot. For example, the computer system can scan the virtual image of the segment of the current RBC loss plot in time across virtual images of reference surgeries until one or a threshold number of matches are identified.

In another implementation, the computer system calculates a linear, quadratic, exponential, logarithmic, or other best-fit trend line for a segment (e.g., a most-recent five minutes) of the current RBC loss plot and compares this best-fit trend line to best-fit trend lines of segments of reference surgeries to identify one or more reference surgery matches. In this implementation, the computer system can shift or scale the trend line for current RBC loss plot in time or in magnitude to map the current RBC loss plot to a reference surgery (or vice versa), such as by a maximum shift of two minutes, by a time scaling factor between 90% and 110%, and by a magnitude scaling factor between 95% and 105%.

In another implementation, in Block S 140, the computer system calculates distances between the current RBC loss plot and reference surgeries of reference surgeries to select one or more matches. In one example, if thirty minutes have elapsed in the current surgery and with a current cumulative RBC loss of 100 mL and 90 mL of RBC volume was lost during a thirty-minute period in a reference surgery, then the computer system can calculate an absolute difference distance metric of 10 mL for the current and reference surgeries. In another example in which the computer system compares RBC volume per unit of surgical textile, if three surgical textiles containing 10 mL, 20 mL, and 40 mL of RBC volume were used during the current surgery and if three surgical textiles containing 10 mL, 30 mL, and 35 mL of RBC volume were used during a reference surgery, then the computer system can calculate an absolute difference distance metric of 15 mL RBC loss for the current and reference surgeries. In this example, the computer system can also weight the sum of differences in RBC loss between the current and reference surgeries based on a timestamp and/or measurement index. In this implementation, in Block S140, the computer system can also compare one or many approximate derivatives of the cumulative RBC loss, such as based on locally-weighted regression or convolution with a linear filter, to calculate a difference between the current surgery and a reference surgery. In another example, in Block S140, the computer system can calculate an Earth Mover's Distance between blood loss events in the current surgery and blood loss events in a reference surgery. Similarly, the computer system can apply a Needleman-Wunsch algorithm and/or a Dynamic-Time-Warping algorithm to match the RBC loss plot from current surgery to a RBC loss period of a reference surgery. In this example, the computer system can align a RBC loss period of a reference surgery to the RBC loss plot of the current surgery by adding gaps to one or both sequences and then calculate a weighted Euclidean distance (or a 1-norm distance, a p-norm distance, or a cosine distance) between parameter vectors for the current and reference surgeries. In this implementation, in Block S140, the computer system can then select one or a limited number of reference surgeries exhibiting a minimal distance from the current surgery. In Block S140, the computer system can additionally or alternatively weight reference surgeries based on corresponding distances from the current RBC loss plot, such as by plugging reference surgery distances into a Gaussian kernel.

In the foregoing implementation in which the computer system implements a Needleman-Wunsch-based algorithm to match the current surgery to a reference surgery in Block S140, the computer system can insert gap into blood loss sequences for the current and/or reference surgeries to account for asynchronicity between the current and reference surgeries, such as to account for paused or delays in blood loss data collection during a reference surgery. The computer system can then manipulate such gaps to choose a point in a matched reference surgery at which the "future" begins and then apply an x-offset to this "future" point of the reference surgery before rendering blood loss data from the reference surgery with blood loss data from the current surgery in Block S150. The computer system can similarly apply a y-offset to blood loss data from the reference surgery to match a RBC loss volume of the matched reference surgery to the RBC loss volume of the current surgery in Block S150. For example, for a reference surgery exhibiting a low distance metric due to a curve shape very similar to that of the current surgery but exhibiting a y-intercept that differs significantly from that of the current surgery, the computer system can implement curve-fitting parameters to add a y-offset to blood loss data from the reference case to better match the current RBC loss volume of the current surgery prior to displaying blood loss data from both the current and the matched reference surgeries in Block S150.

The computer system can thus select a single reference surgery or a minimum number of (e.g., two) reference surgeries that best match(es) the selected segment of the current reference surgery, such as shown in FIG. 1D. Similarly, the computer system can select all reference surgeries that deviate from the current RBC loss plot by less than a threshold degree (e.g., 5%) over the duration of the processed segment of the current RBC loss plot.

In one implementation, in Block S140, the computer system flags one or more trigger events in the current RBC loss plot and compares the time, magnitude and/or type of the trigger event to trigger events of reference surgeries to identify one or more matches for the current RBC loss plot. For example, the computer system can flag: a time in the current RBC loss plot at which an RBC volume greater than a threshold RBC volume is lost by the patient; a time at which the patient exhibits greater than a threshold rate or RBC loss or exhibits a rapid increase or decrease in rate of RBC loss; a time at which the patient's intracirculatory Ht drops below a threshold Ht, as described below; a time at which the patient's volemic status deviates from euvolemia by more than a threshold deviation, as described below); a time at which an autologous or allogeneic blood infusion is initiated); a time at which a saline infusion is initiated; time of identification of a further patient complication; a time at which the patient enters cardiac arrest; at time at which the surgery is completed; and/or a time of any other measurable or identified surgical event.

In the foregoing implementation, the computer system can then match the current reference surgery to one or a limited number of reference surgeries by comparing trigger events between the current RBC loss plot and reference surgeries. For example, the computer system can identify a set of reference surgeries characterized by a similar set, order, and/or magnitude of trigger events and can then match the current RBC loss plot to one or a subset of the set of reference surgeries by implementing template matching or parametric techniques, as described above. The computer system can additionally or alternatively identify a primary trigger event in the current RBC loss plot and process only a segment of the current RBC loss plot succeeding the trigger event (inclusive or exclusive) for matching to reference surgeries. The computer system can also limit comparisons of the segment of the current RBC loss plot to segments of reference surgeries preceded by similar trigger events (e.g., trigger events of similar types and/or magnitudes).

In Block S140, the computer system can also filter out historic RBC loss periods—such as from a database of reference surgeries—to remove from consideration reference surgeries that may be substantially unrelated to the current RBC loss plot and to prioritize reference surgeries for comparison to the current RBC loss plot. For example, the computer system can filter reference surgeries by patient demographic, such as age, gender, weight, and/or medical history of the patient. The computer system can filter reference surgeries by surgery type, surgeon, hospital, operating room, time of day, location or region, and/or any other parameter.

The computer system can also normalize the current RBC loss plot to similarly-normalized reference surgeries. For example, prior to comparing a segment of the current RBC loss plot to reference surgeries, the computer system can shift RBC loss magnitudes, relative timings of blood loss events, and/or thresholds definitions for trigger events, etc. based on patient demographic and/or other surgical parameters 5. Blood Loss Projection Block S150 of the method S100 recites extending the plot of blood component loss by the patient in the user interface into a future time with blood component loss data from the reference surgery; and Block S160 of the method S100 recites rendering markers for an action and an event occurring during the reference surgery with the plot of blood component loss by the patient in the user interface. Generally, the computer system can execute Blocks S150 and S160 to project future RBC loss of patient, subsequent trigger events, and an outcome of the surgery based on one or more matched reference surgeries and to present these projections in real-time through a user interface for review by a user (e.g., a nurse, a surgeon, an anesthesiologist).

In one implementation, the computer system plots RBC loss data for the patient during the current surgery up to a most-recent blood loss event (i.e., the "current RBC loss plot") in Block S140 and then extends the current RBC loss plot with RBC loss data from a matched reference surgery (hereinafter "plot extension") in Block S150. The computer system can also insert—into the plot extension—markers for significant actions and events recorded during the corresponding reference surgery in Block S160. For example, the computer system can retrieve intravenous infusion data for the reference surgery associated with the plot extension, such as: infusion flow rates; infusion start and stop times; total infusion volume; infused fluid type including colloids (e.g., allogeneic or autologous blood or blood components), crystalloids (e.g., saline, an anti-clotting agent, lactated Ringer's solution), and/or volume expanders; cell salvage start time, preparation time, and salvaged volume; and/or infused fluid quality (e.g., Ht, chemical composition), etc. In this example, the computer system can then add to the plot extension—extending from the current RBC loss plot for the current surgery—markers for infusion events that occurred during the reference surgery. In another example, the computer system can retrieve data for surgical events that occurred during the reference surgery, such as rapid changes in patient RBC loss rate, identification of other patient complications, cardiac arrest, or completion of the surgery; and the computer system can add markers for such surgical events into the plot extension for the current surgery. In yet another example, the computer system can add a marker or a note to the tail of the plot extension based on a final outcome and/or post-operative data from reference surgery, such as: the success of the reference surgery (e.g., whether a repeat surgery was necessary, whether the patient died or developed further complications); patient recovery time after the reference surgery (e.g., inpatient or outpatient recovery duration); total cost of the reference surgery; total time of the reference surgery; total volume of infused allogeneic blood during the reference surgery; the total amount (e.g., mass, volume) of salvaged RBCs or ratio of salvaged to abandoned RBCs during the reference surgery; etc.

Therefore, as in the previous examples, the computer system can augment real patient RBC loss data from the current surgery with RBC loss data from a reference surgery, including the time and magnitude of blood loss events, infusion-related actions, and other actions and events that occurred during the reference surgery.

As shown in FIG. 1E, the computer system can also render multiple plot extensions—from RBC loss periods from multiple reference surgeries —with the RBC loss plot for the current surgery in Block S150, and the computer system can add one or more event markers, action markers, and/or final outcome markers to each plot extension, as described above, in Block S160. For example, the computer system can add four plot extensions corresponding to four distinct reference surgeries, wherein the four plot extensions (approximately) intersect the final point in RBC loss plot for the current surgery but divert into distinct outcomes. In this example, the computer system can add action, event, and outcome markers to each of the four plot extensions to provide dynamic and real-time insight into the effect that various types and times of actions may affect the type and times of surgical events during the current surgery and the final outcome of the surgery. A surgeon, nurse, or anesthesiologist can therefore review the current RBC loss plot, the various plot extensions, and the markers inserted into the plot extensions to predict future patient RBC losses of the patient, to determine which actions to take and which to avoid, and when to take various actions (cell salvage, saline infusion) during the surgery.

In one variation, the computer system also selects a preferred plot extension (or a preferred subset of the rendered plot extension) from a matched reference surgery, such as based on total RBC loss across the plot extension or based on a final outcome of the corresponding surgery (e.g., success, total transfused blood volume, and/or total time of the reference surgery, etc.). In this variation, the computer system can highlight the preferred plot extension in the user interface and/or trigger (audible and/or visual) prompts during the surgery to execute actions to maintain (or better) the pace of the preferred plot extension. In particular, the computer system can correlate an action in the reference surgery with a positive event occurring during the reference surgery or a positive outcome of the reference surgery, and the computer system can serve—to the operating room during the current surgery—a prompt for an action exhibiting a strong correlation to a positive event or to a positive outcome in the reference surgery. In various examples, the computer system can serve and audible and vision prompt to the operating room to initiate a saline infusion, to prepare for cell salvage, to retrieve allogeneic blood, and to initiate a blood infusion at a particular infusion rate, etc. based on times of similar action markers noted in the preferred plot extension.

In this variation, the computer system can similarly identify an undesirable plot extension for a matched reference surgery and can deliver a prompt during the current surgery to avoid a particular action (or to avoid a particular action at a particular time or within a particular time window) for an action exhibiting a strong correlation to a negative event during the reference surgery or to a negative outcome of the reference surgery.

Figure 5:
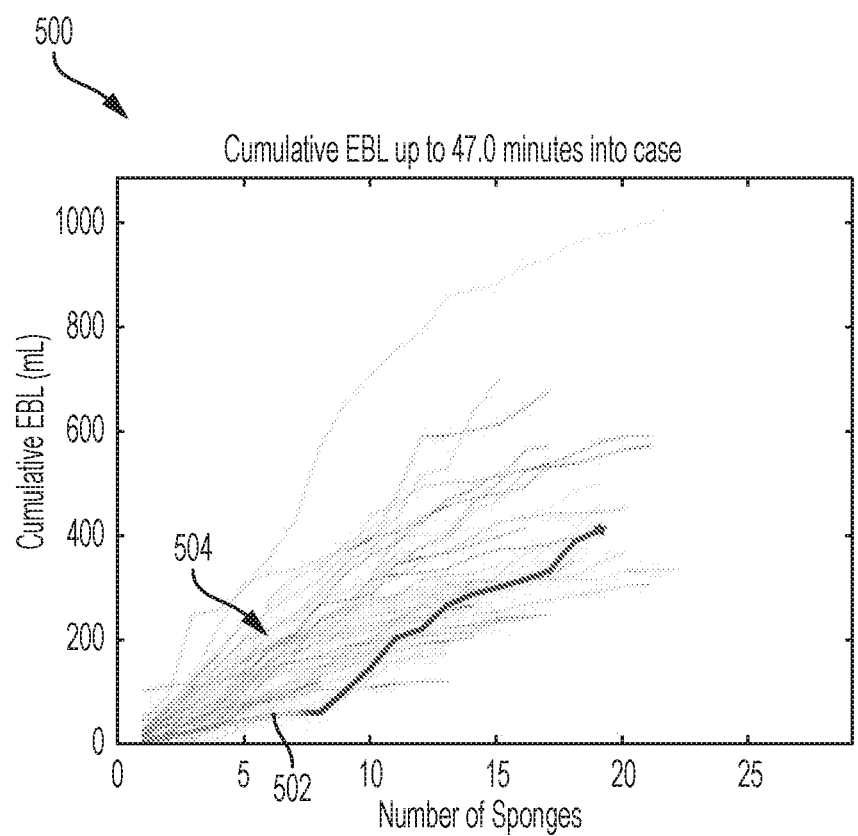
FIG. 5 is a graphical representation of one variation of the method.

In Block S150, the computer system can additionally or alternatively plot RBC loss data from matched reference surgeries over a duration of the plot between the start time of the current surgery to the current time, as shown in FIG. 5. In one implementation, the computer system renders the RBC loss plot for the current surgery with RBC loss data from reference surgeries up to a reference time (corresponding to the current time in the current surgery), such as to provide a real-time visual comparison between the current surgery and previous surgeries. For example, the computer system can render RBC loss data from one or more reference surgeries on the same plot as RBC loss data from the current surgery. The computer system can also render both a vertical "lane plot" including an estimated current cumulative total RBC loss for the current surgery and a histogram of cumulative RBC loss at the current time or at a current container index (i.e., a count of used surgical textiles, as described below) for the current surgery. Furthermore, the computer system can compute and display a "bleeding index" metric, such as a percentile of the current cumulative RBC loss of the patient relative to a cumulative RBC loss at the same time and/or at the same container index for one or more reference surgeries. In this implementation, the computer system can also align RBC loss data in the time domain or in the container index domain such that RBC loss data at a particular time in the current surgery is compared to RBC loss data from a different time in a reference surgery, such as by implementing a Needleman-Wunsch or Dynamic Time Warping algorithm.

In Block S150, the computer system can additionally or alternatively render a bleeding rate metric, such as to provide additional visual feedback related to the rate of blood loss (or RBC mass or volume) by the patient. For example, the computer system can render an instantaneous bleeding rate (i.e., a derivative), an overall average bleeding rate (i.e., a current cumulative RBC loss volume (or mass) divided by a time duration or container index sum for the current surgery), an average bleeding rate over the last n seconds or over the last n container indexes, etc. In this implementation, the computer system can apply locally weighted linear regression, fit a linear trend line to the last n points, apply a Sobel filter to the smoothed RBC loss plot, and/or implement a Kalman filter including a bleeding rate in its hidden state, etc.

6. Volemic Status Projection

In one variation, the computer system implements similar methods and techniques to: track a volemic status (e.g., deviations from euvolemia) of the patient; generate a patient volemic status plot for the current surgery based on blood loss events and infusion events during the surgery; match the volemic status plot for the current surgery to a volemic status plot from a reference surgery; and extend the volemic status plot for the current surgery with volemic status data from the matched reference surgery.

In this variation, the computer system can track the patient's volemic status over time by transforming blood loss and transfusion events into deviations from euvolemia. For example, before or at the beginning of the surgery, the computer system can estimate the initial circulatory volume of the patient based on the patient's age, weight, gender, or other demographic. In this example, the computer system can also estimate the total circulatory fluid loss for each blood loss event by combining a measured or estimated Ht value of the patient at or around the time of the blood loss event with the RBC volume (or mass) estimate for the bloodied container corresponding to the blood loss event and then update the estimate circulatory volume of the patient by subtracting the circulatory fluid loss estimate for each subsequent blood loss event from a last patient circulatory volume estimate (beginning with the initial circulatory volume). The computer system can also estimate a volume of the total circulatory volume of the patient that is naturally absorbed out of the patient's circulatory system between a previous blood loss event and a current blood loss event—such as based on a static circulatory absorption rate and a duration between the blood loss events—and then subtract this volume from the total estimated patient circulatory volume for the current blood loss event. The computer system can also track volumes of fluids infused into the patient during the surgery and update the estimated circulatory volume of the patient accordingly.

The computer system can then calculate a difference between the initial circulatory volume (or the preferred circulatory volume of the patient) and the estimated circulatory volume of the patient after each blood loss event to calculate a volemic status of the patient for each blood loss event. In this variation, the computer system: plots these volemic statuses throughout the surgery; implements template matching and/or parametric techniques to identify one or more reference surgeries characterized by similar volemic status changes over time, as described above; extends the patient volemic status plot for the current surgery with volemic status data from the reference surgery; adds markers to the volemic status plot extension; and renders these data substantially in real-time during the current surgery, such as described above.

7. Hematocrit Projection

In one variation, the computer system implements similar methods and techniques to: track the patient's hematocrit (Ht) based on blood loss events and infusion events during the surgery; generate a patient Ht plot for the current surgery; match the Ht plot for the current surgery to a Ht plot from a reference surgery; and extend the Ht plot for the current surgery with Ht data from the matched reference surgery.

In this variation, the computing device can transform the RBC loss plot for the current surgery into a hematocrit (Ht) plot for the patient based: on an initial Ht of the patient at the start of the surgery; infusion volumes, rates, and fluid qualities; and/or estimated circulatory absorption rate of the patient. For example, the computer system can retrieve an initial Ht measurement for the patient manually entered by a nurse at the start of the surgery, or the computer system can predict an initial Ht of the patient based on the patient's demographic (e.g., 40% Ht for a female patient, 45% Ht for a male patient). The computer system can then estimate the patient's Ht for each subsequent blood loss event based on: the preceding Ht estimate; an estimated change in the patient's circulatory volume since the last blood loss event, including saline infusions, which may reduce Ht, and allogeneic and autologous blood infusions, which may increase or decrease patient Ht depending on relative Ht of the infused volume. In this example, the computer system can apply a default estimated Ht for volumes of transfused allogeneic blood (e.g., 42.5%) or read an Ht value from a barcode applied to the blood infusion bag. For autologous blood infusions, the computer system can prompt a user to enter a volume or mass of recycled RBCs and a volume of saline (or other fluid) mixed with the recycled RBCs in preparation for infusion. From these data, the computer system can calculate the patient's Ht at discrete blood loss events throughout the surgery.

In this variation, the computer system then: plots these Ht values over time; implements template matching and/or parametric techniques to identify one or more reference surgeries characterized by similar Ht changes over time, as described above; extends the patient Ht plot for the current surgery with Ht data from the reference surgery; adds markers to the Ht plot extension; and renders these data substantially in real-time during the current surgery, such as described above.

In the foregoing variations, the computer system can present various distinct plots to a user during the surgery, such as one RBC loss plot, one volemic status plot, one Ht loss plot, and/or one cumulative blood volume loss plot. The computer system can also combine two data types (e.g., RBC loss data and volemic status data) into a single virtual graphic and then render this virtual graphic on a display within the operating room for review by a user. The computer system can also the current surgery to a reference surgery based on multiple distinct data types, such as volemic status and Ht.

The computer system can also store RBC loss data, volemic status, Ht data, surgical actions surgical activities, and/or surgery results, etc. of the current surgery in the database of reference surgeries for matching to a subsequent surgery, such as according to the method and techniques described above.

8. Surgical Textiles

In one variation of the method, the computer system tracks RBC (or hemoglobin or whole blood) content in each of a contiguous sequence of surgical textiles (e.g., five surgical textiles) used during the current surgery, generates a plot of cumulative RBC content in the contiguous sequence of surgical textiles for the current surgery, and matches the RBC content plot for the current surgery to the RBC content plot of one or more reference surgeries (i.e., reference surgeries), such as by implementing methods and techniques described above. The computer system then incorporates RBC loss data from one or more matched reference surgeries to the RBC content plot of the current surgery in Block S150, as shown in exemplary FIGS. 4, 5, 6, 7, and 8.

Figure 4:
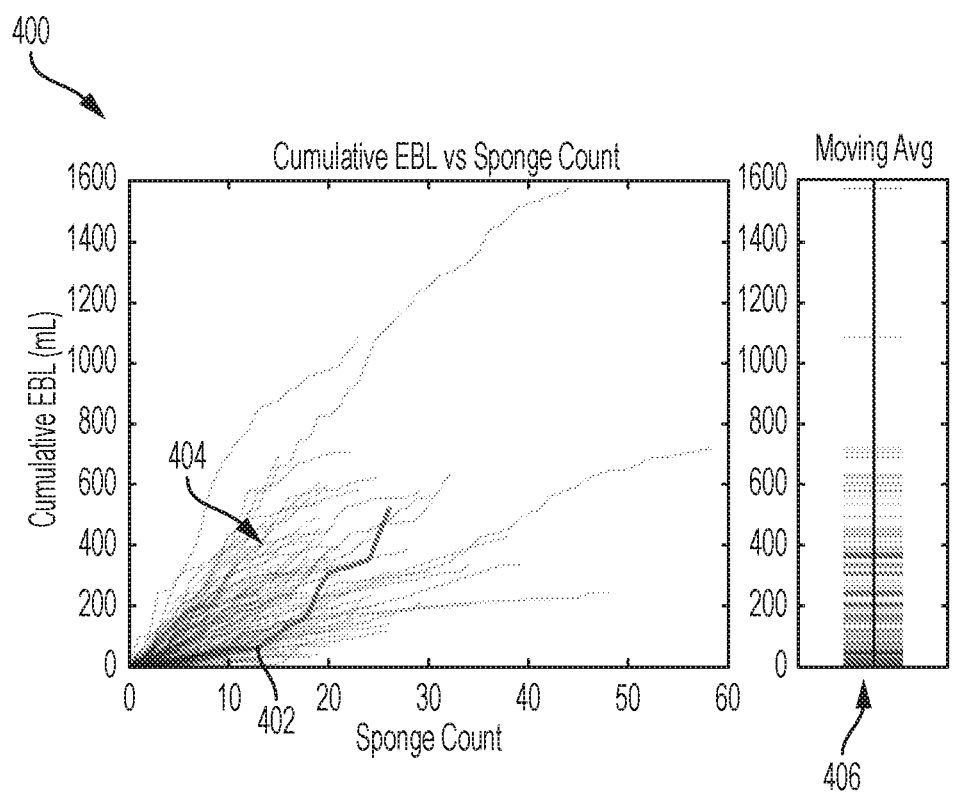
FIG. 4 is a graphical representation of one variation of the method.

FIG. 4, for example, depicts the current cumulative estimated blood loss over a sponge count, rather than over time, but could also be depicted over time. The computer system may provide a display 400 that includes the current surgical procedure depicted as thickened line 402, while one or more reference cases may be depicted as thinner lines 404. In this plot, each scanned sponge represents one count, but in other embodiments, a plurality of different blood retention structures may be normalized or transformed into equivalent count values. The display 400 may optionally include a plot 406 of the moving average or cumulative average of the current surgical procedures and the references surgical procedures may also be provided 8. Confidence Interval As noted above, in the variation of the methods in which the computer system processes blood loss events over time, the computer system can aggregates reference surgeries from a set of matched reference surgeries into a range of RBC loss volumes for each blood loss event—up to a current time—in the current surgery. The computer system can also aggregate reference surgeries from the set of matched reference surgeries into a range of projected RBC loss volumes for a future period of time during the surgery. For example, in Block S150, the computer system can generate a confidence interval history for RBC loss data from the reference surgeries over the current duration of the surgery and into the future and then plot RBC loss bounds of this confidence interval history over time for alongside RBC loss data over time for the current surgery in Block S150.

The confidence intervals may be calculated in a number of ways. In one example, if a non-parametric prediction method used, the confidence interval can be based on the statistics of known curves or data sets in the database that are similar to the available curve or data of the current surgical procedure. For example, if the prediction is an average of the K nearest neighbors, then the confidence interval could be an exemplary interval of two standard deviations, i.e. 1.96 standard deviations around that average, or it could literally be a confidence interval of the sample mean of the K neighbors (i.e. based on a t-distribution). In other variations, a different number of standard deviations may be used, e.g. ±0.55 D, ±1 SD, ±1.5 SD, for example. In another example, if the nonparametric method uses a kernel to get a weighted average, those same kernel weights could be used to compute the statistics for the confidence interval. In still another example, if a parametric prediction method is being used, then the confidence interval of the fitted model could be used to compute the confidence of the prediction. For example, if a probabilistic method such as a Kalman filter is being used, then the probability distribution of the hidden state could be used to compute a probability distribution over the predictions, and the confidence interval could be the middle 95% probability mass of that distribution. In another embodiment, where a formula is being fitted to past estimated blood loss measurements, then standard statistical methods could be used to compute a confidence interval around the fitted line. In addition, for any prediction method being used, the accuracy of that method could be directly evaluated and used to compute a confidence interval. For example, a holdout set could be designed specifically to measure the bias and standard deviation of the prediction errors, which in turn could be used to construct an interval around any prediction. Or during an ongoing case, prediction errors from the past could be used to compute a confidence interval for the future (e.g. if N measurements have been taken, then predict the last K points from the first N-K points and use those prediction errors for a confidence interval). Finally, a confidence interval formula could be explicitly learned from a large amount of data, using standard machine-learning techniques.

FIG. 5 depicts another metric or plot that is optionally provided. Here, the display 500 simultaneously depicts the cumulative estimated blood loss and the number of sponges of the current case 502 and the reference cases 504, indexed to the current time point of the current case. Thus, the reference case 504 tracing are revealed over time as the current time progresses.

Figure 6:
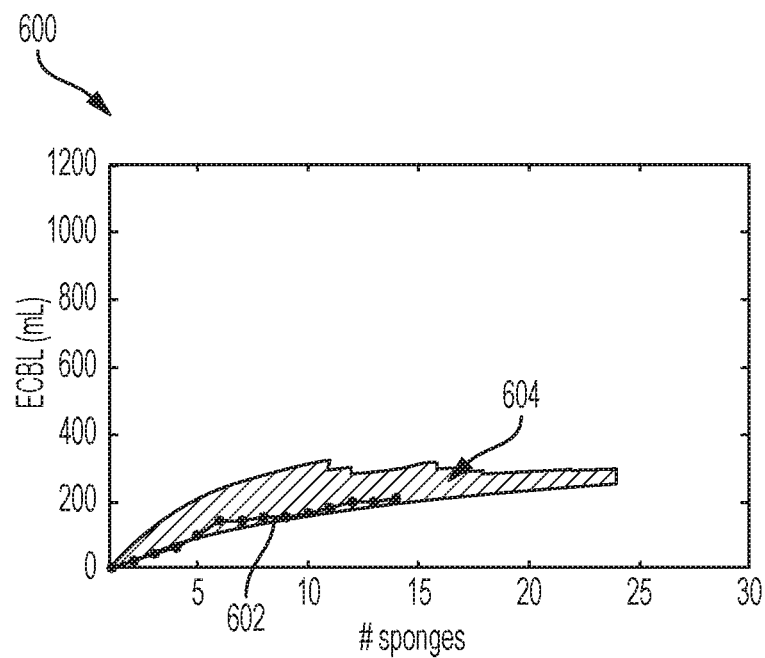
FIG. 6 is a graphical representation of one variation of the method.
Figure 7:
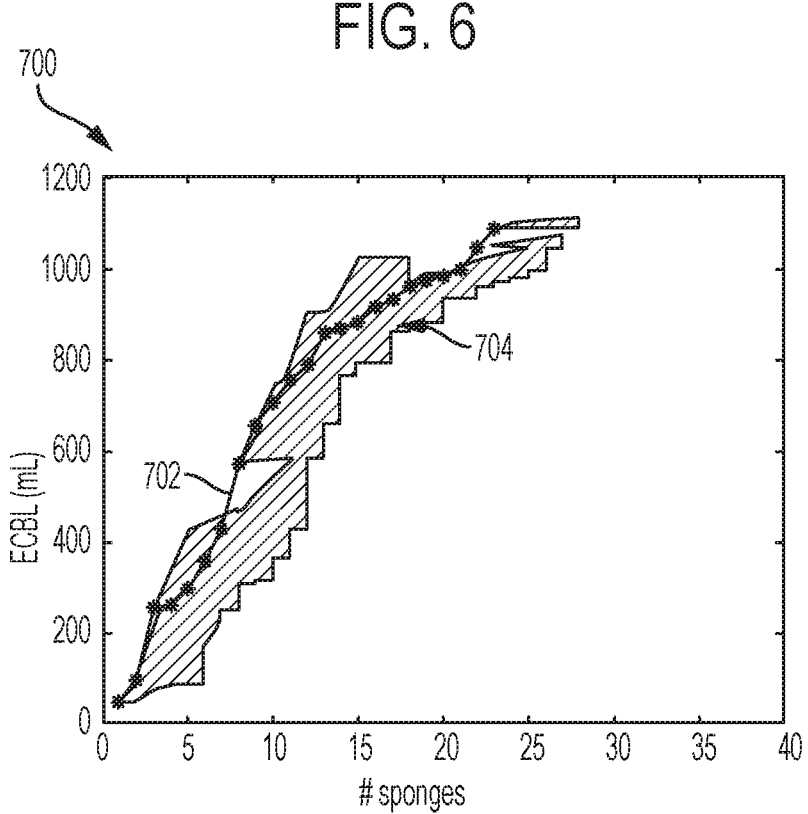
FIG. 7 is a graphical representation of one variation of the method.
Figure 8:
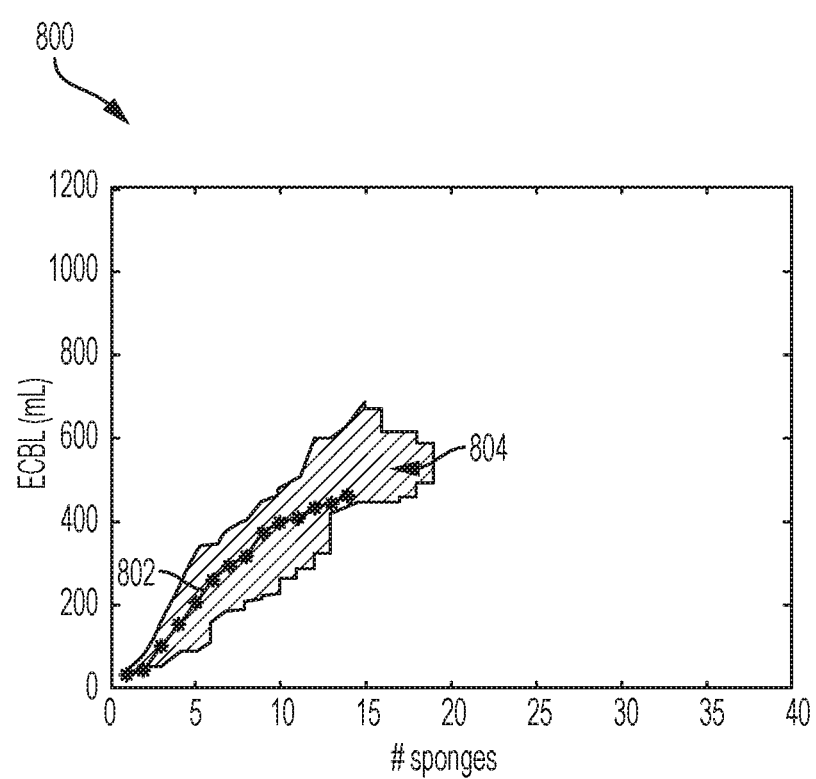
FIG. 8 is a graphical representation of one variation of the method.

FIG. 6 depicts another example of a display screen 600, which also simultaneously depicts the cumulative estimated blood loss and the number of sponges or other unit measure of the current surgical procedure 602, but instead of depicting the corresponding reference case tracings as in FIG. 5, a shaded region 604 is provided to show the confidence interval of the predicted future estimated blood loss, which is described in greater detail below. FIGS. 7 and 8 illustrate display screens 700, 800 also simultaneously depicting the cumulative estimated blood loss and the number of sponges, but for different current surgical procedures 702, 802 that have a higher relative blood loss, and a lower relative blood loss, respectively, with corresponding confidence interval regions 704, 804, but at a different time point than that depicted in FIG. 6.

Figure 2A:
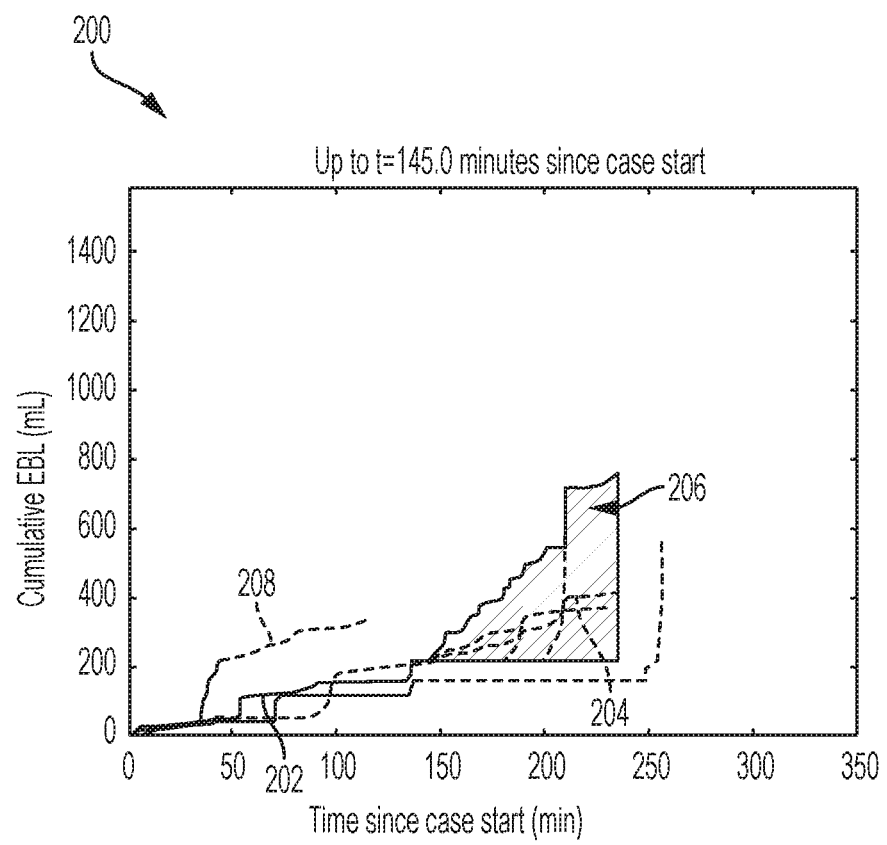
FIG. 2A and 2B are graphical representations of one variation of the method, depicting a surgical procedure at different points in time.
Figure 2B:
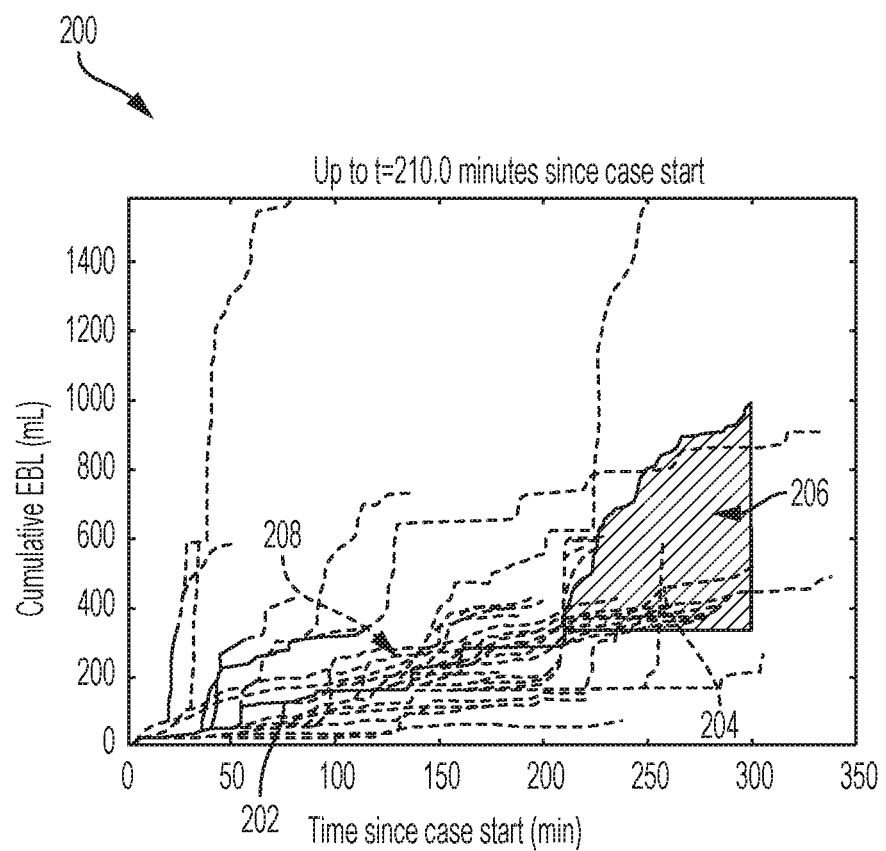

Alternatively, the computer system can generate a prediction range for RBC loss from a current time in the surgery into the future based on RBC loss data from multiple reference surgeries matched to the current surgery. For example, in FIG. 2A, the computer system can calculate and provide a display 200 of a 95% limits-of-agreement range (or other percentage range) according to a weighted standard deviation for the reference surgeries matched to the current surgery and then plot this range extending from the RBC loss at the current time in (or most recent blood event of) the current surgery, as shown in FIG. 2A. The thickened solid line 202 depicts the current surgical procedure from the start of the procedure to the current time, while the dashed thickened line 204 depicts the predicted blood loss for a period of time in the future, which is 90 minutes in the exemplary embodiment, but could be a different size time period from 5 minutes to 5 hours, or greater, or until the predicted end of the surgery. Thus, the estimates may include both the final estimated blood loss, as well as interim estimates of blood loss. The shaded region 206 in this example is a 95% limits-of-agreement range using a weighted standard deviation. The reference cases or data sets selected from the database are depicted in the lighter dashed lines 208. FIG. 2B depicts the same surgical procedure and reference data, but redrawn to reflect the further passage of time and additional measured blood loss.

Figure 2C:
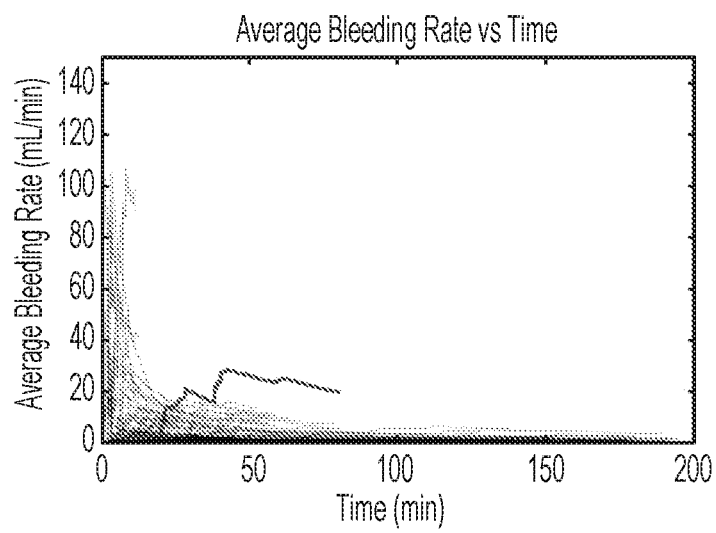
FIGS. 2C and 2D are graphical representation of average and instantaneous bleeding rates over time.
Figure 2D:
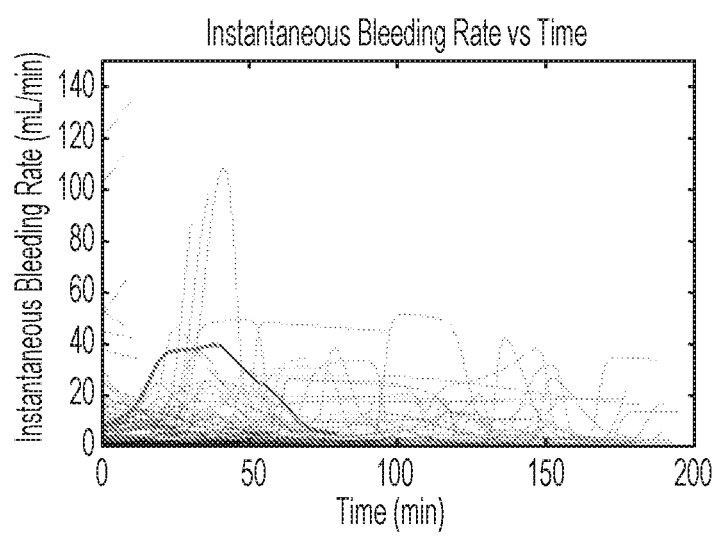

In addition to depicting the cumulative estimated blood loss over time, the time information associated with the current and reference surgical procedures may also be used to depicted, for example, the average bleeding rate over time, as shown in FIG. 2C, or the instantaneous bleeding rate, as shown in FIG. 2D. The instantaneous bleeding rate may be estimated as the slope from a locally weighted linear regression.

Similarly, in the variation of the method in which the computer system processes RBC losses (or Ht change, volemic status change, cumulative blood loss, etc.) for each of a contiguous sequence of surgical textile used during the surgery, the computer system can aggregates RBC losses from matched contiguous sequences of surgical textiles used in reference surgeries into a range of cumulative RBC loss volumes per surgical textile count up to a total number of surgical textiles counted as used during the current surgery. The computer system can also aggregate RBC losses from the contiguous sequences of surgical textiles from reference surgeries into a range of projected RBC loss volumes per additional used surgical textile beyond the current count of used surgical textiles in the current surgery. For example, in Block S150, the computer system can generate a confidence interval history for cumulative RBC loss data per additional surgical textile from the reference surgeries for up to and beyond the current number of surgical textiles used in the current surgery and then plot RBC loss bounds of this confidence interval history per additional surgical textile unit alongside RBC loss data per additional surgical textile unit for the current surgery in Block S150, as shown in FIGS. 6, 7, and 8.

The systems and methods of the embodiments can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a user computer or mobile device, wristband, smartphone, or any suitable combination thereof. Other systems and methods of the embodiment can be embodied and/or implemented at least in part as a machine configured to receive a computer-readable medium storing computer-readable instructions. The instructions can be executed by computer-executable components integrated by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor but any suitable dedicated hardware device can (alternatively or additionally) execute the instructions.

As a person skilled in the art will recognize from the previous detailed description and from the figures and claims, modifications and changes can be made to the embodiments of the invention without departing from the scope of this invention as defined in the following claims.

What is claimed is:

1. A method of monitoring a patient in a medical procedure, comprising:
   at one or more processors:
   estimating real-time blood loss of the patient;
   selecting at least one reference blood loss data set corresponding to a reference medical procedure;
   estimating future blood loss of the patient based at least partially on the estimated real-time blood loss and the at least one reference blood loss data set; and
   providing an indication of the estimated future blood loss of the patient on a display associated with the one or more processors.

2. The method of claim 1, wherein selecting at least one reference blood loss data set comprises selecting at least one reference blood loss data set from a database of prior medical procedures.

3. The method of claim 1, wherein the indication of estimated real-time blood loss and the estimated future blood loss are displayed simultaneously on a monitor screen.

4. The method of claim 1, further comprising displaying the estimated real-time blood loss and the indication of estimated future blood loss on a two-dimensional plot.

5. The method of claim 4, wherein the two-dimensional plot depicts estimated blood loss over time.

6. The method of claim 4, further comprising displaying the at least one reference blood loss data set on the two-dimensional plot.

7. The method of claim 6, wherein displaying the at least one reference blood loss data set comprises displaying at least one blood loss tracing over time.

8. The method of claim 7, wherein each of the at least one blood loss tracings is based upon a single historical medical procedure.

9. The method of claim 8, wherein displaying the at least one reference blood loss data set comprises displaying a plurality of database blood loss tracings over time.

10. The method of claim 6, wherein the at least one reference blood loss data set is provided as at least one band plot on the two-dimensional plot.

11. The method of claim 10, wherein the at least one band plot comprises a plurality of nested confidence bands on the two-dimensional plot.

12. The method of claim 6, wherein the estimated real-time blood loss and the estimated future blood loss are overlaid on the at least one reference blood loss data set.

13. The method of claim 1, further comprising receiving the at least one reference blood loss data set from a remote server.

14. The method of claim 1, wherein selecting the at least one reference blood loss data set is based at least in part upon type of medical procedure.

15. The method of claim 1, wherein selecting the at least one reference blood loss data set is based at least in part upon one or more patient factors.

16. The method of claim 15, wherein selecting the at least one reference blood loss data set is based at least in part upon one or more health condition or disease factors, or practice-based factors.

17. The method of claim 16, wherein the at least one reference blood loss data set comprises an average, median, mode or a range of historical blood loss values from a plurality of prior medical procedures.

18. The method of claim 17, wherein each of the plurality of prior medical procedures is a same type of procedure as the medical procedure.

19. The method of claim 18, wherein the plurality of prior medical procedures are medical procedures selected based upon n blood loss tracings closest to a curve-of-best-fit of a current blood loss tracing that includes the estimated real-time blood loss.

20. The method of claim 19, wherein n is between 2 and 50.

21. The method of claim 19, wherein n is between 2 and 10.

22. The method of claim 1, further comprising:
   comparing the estimated real-time blood loss to a threshold value; and
   displaying a message if the estimated real-time blood loss meets or exceeds the threshold value.

23. The method of claim 22, wherein the threshold value is a time-dependent threshold value.

24. The method of claim 22, wherein the threshold value is based on the at least one reference blood loss data set.

25. The method of claim 22, wherein the message is a clinical message indicating that a blood transfusion threshold has been met.

26. The method of claim 22, wherein the message is a clinical message indicating that a blood transfusion threshold is estimated to be met at a future time point.

27. The method of claim 1, wherein estimating future blood loss comprises providing at least two predicted future blood loss values, wherein one of the least two predicted future blood loss values is a lower limited predicted future blood loss value.

28. The method of claim 27, wherein one of the at least two predicted future blood loss values is an upper limited predicted future blood loss value.

29. The method of claim 1, wherein providing the indication of the estimated future blood loss comprises displaying a predicted future blood loss area plot.

30. The method of claim 1, wherein estimating real-time blood loss comprises estimating real-time blood loss based on at least one image.

31. The method of claim 30, wherein estimating real-time blood loss comprises evaluating a color-related value of the at least one image.

32. The method of claim 1, wherein estimating real-time blood loss comprises aggregating a plurality of real-time blood loss estimates from two or more images.

* * * * *

UNITED STATES PATENT AND TRADEMARK OFFICE
CERTIFICATE OF CORRECTION

PATENT NO. : 10,555,675 B2
APPLICATION NO. : 15/154921
DATED : February 11, 2020
INVENTOR(S) : Satish et al.

Page 1 of 1

It is certified that error appears in the above-identified patent and that said Letters Patent is hereby corrected as shown below:

In the Specification

In Column 10, Line 15, delete "a" and insert --of-- therefor

Signed and Sealed this
Twenty-ninth Day of September, 2020

Andrei Iancu
*Director of the United States Patent and Trademark Office*